United States Patent [19]
Verostko et al.

[11] Patent Number: 5,792,621
[45] Date of Patent: Aug. 11, 1998

[54] FIBER-OPTIC CHEMILUMINESCENT BIOSENSORS FOR MONITORING AQUEOUS ALCOHOLS AND OTHER WATER QUALITY PARAMETERS

[75] Inventors: Charles E. Verostko, Houston, Tex.; James E. Atwater, Eugene, Oreg.; James R. Akse, Roseburg, Oreg.; Jeffrey L. DeHart; Richard R. Wheeler, both of Myrtle Creek, Oreg.

[73] Assignee: The United States of America as represented by the Administrator of the National Aeronautics and Space Administration, Washington, D.C.

[21] Appl. No.: 496,230

[22] Filed: Jun. 28, 1995

[51] Int. Cl.$^6$ ............................. C12Q 1/54; C12Q 1/28; C12Q 1/26; G01N 21/76

[52] U.S. Cl. ............................. 435/14; 435/25; 435/28; 435/283.1; 435/289.1; 435/290.1; 435/287.1; 435/288.7; 435/968; 435/4; 436/68; 436/63; 436/74; 422/50; 422/52; 422/68.1

[58] Field of Search ............................. 435/14, 25, 28, 435/283.1, 289.1, 290.1, 4, 287.1, 288.7, 968; 436/68, 63, 74; 422/50, 52, 68.1

[56] References Cited

U.S. PATENT DOCUMENTS

| | | | |
|---|---|---|---|
| 3,902,970 | 9/1975 | Levin | 195/103.5 C |
| 4,353,983 | 10/1982 | Siddiqi | 435/11 |
| 4,556,635 | 12/1985 | Hitzman et al. | 435/25 |
| 4,929,561 | 5/1990 | Hirschfeld | 436/116 |
| 5,160,604 | 11/1992 | Nakamura et al. | 210/85 |
| 5,176,881 | 1/1993 | Sepaniak et al. | 422/82 |
| 5,194,393 | 3/1993 | Hugl et al. | 436/525 |
| 5,272,088 | 12/1993 | Morlotti | 436/68 |

OTHER PUBLICATIONS

Blum, Loic J; "Enzyme Microb. Technol."; vol. 15(5), pp. 407–411, (1993) month not available.

"Highly Stable First–Generation Biosensor for Glucose Utilizing Latex Particles as the Enzyme–Immobilizing Matrix," C. G. J. Koopal & R. J. M. Nolte, *Enzyme Microb. Technol.*, 1994, vol. 16, May, pp. 402–408.

"Peroxidase– and Tetracyanoquinodimethane–Modified Graphite Paste Electrode for the Measurement of Glucose/Lactate/Glutamate Using Enzyme–Packed Bed Reactor," P. C. Pandey & H. H. Weetall, *Analytical Biochemistry* 224, 428–433 (Jan. 1995).

"A Chemiluminescence Fiber–Optic Biosensor System for the Determination of Glutamine in Mammalian Cell Cultures," M. V. Cattaneo, K. B. Male, & J. H. T. Luong, *Biosensors & Bioelectronics*, vol. 7, (1992) pp. 569–574.

"On Line Chemiluminescence Assay Using FIA and Fiber Optics for Urinary and Blood Glucose," M. V. Cattaneo and J. H. T. Luong, *Enzyme Microb. Technol*, 1993, vol. 15, May pp. 424–428.

"Fiber–Optic Biosensor for Hypoxanthine and Xanthine Based on a Chemiluminescence Reaction," J. Hlavay, S. D. Haemmerli & G. G. Guilbault, *Biosensors & Bioelectronics*, vol. 9, 1994, pp. 189–195.

*Primary Examiner*—Louise Leary
*Attorney, Agent, or Firm*—Hardie R. Barr

[57] ABSTRACT

A "reagentless" chemiluminescent biosensor and method for the determination of hydrogen peroxide, ethanol and D-glucose in water. An aqueous stream is basified by passing it through a solid phase base bed. Luminol is then dissolved in the basified effluent at a controlled rate. Oxidation of the luminol is catalyzed by the target chemical to produce emitted light. The intensity of the emitted light is detected as a measure of the target chemical concentration in the aqueous stream. The emitted light can be transmitted by a fiber optic bundle to a remote location from the aqueous stream for a remote reading of the target chemical concentration.

18 Claims, 15 Drawing Sheets ately 5,792,621

FIBER-OPTIC CHEMILUMINESCENT BIOSENSORS FOR MONITORING AQUEOUS ALCOHOLS AND OTHER WATER QUALITY PARAMETERS

ORIGIN OF THE INVENTION

The invention described herein was made in the performance of work under a NASA contract and is subject to the provisions of Section 305 of the National Aeronautics and Space Act of 1958, Public Law 85-568 (72 Sat. 435; 42 U.S.C. 2457).

SUMMARY OF THE INVENTION

Fiber optic chemiluminescent biosensors embody a "reagentless" technology for quantitation of ethanol and other important water quality parameters with extremely low detection limits. Sensor operation is based upon the enzymatic oxidation of ethanol (or other target species) to produce hydrogen peroxide, which then reacts with luminol to produce light. The light intensity is measured by a photomultiplier tube. The light emitting reactions are promoted using immobilized enzymes and solid state flow-through modules which contain the required reactants. The luminescent reactions are electrically catalyzed.

The unit operations required for sensor operation include pH adjustment using solid phase flow-through modules, immobilized enzyme catalyzed oxidation of ethanol and glucose to hydrogen peroxide, controlled release of luminol using a solid phase flow-through module, electrocatalyzed luminescence using a potentiostat and gold electrodes, fiber optic transmission of chemiluminescent emissions, and quantification of light intensity using a photomultiplier tube.

Calibration curves for ethanol, D-glucose, and hydrogen peroxide have been generated using fully integrated reagentless test systems. See FIGS. 22–25. Using the immobilized enzyme alcohol oxidase, aqueous ethanol concentrations have been determined in the range between 0 and 4,000 µg/L (ppb) as carbon (C). Levels down to 40 µg/L (ppb) of ethanol have been detected. An order of magnitude improvement in sensitivity is possible. Using glucose oxidase, a calibration curve for D-glucose was developed over the concentration range between 0 and 100 mg/L (ppm). The enzyme catalyzed reaction rates for this system were found to be significantly slower than for the alcohol oxidase system. A calibration curve for $H_2O_2$ was obtained between 0 and 18,000 µg/L. Detection of $H_2O_2$ is critical to the functioning of all of the fiber optic chemiluminescent biosensors. Using appropriate oxidase enzymes which catalyze the production of $H_2O_2$, the technique can be extended to provide selective and sensitive detection of other target species such as, for example, 1,2-propanediol, ethylene glycol, glycolic acid, lactic acid and the like.

The innovative technology of this invention is useful in both flight water quality monitoring abroad spacecraft, and in on-line monitoring of ethanol and glucose for control of fermentation bioreactors in brewing, pharmaceutical, and other biotechnological applications.

The Fiber Optic Chemiluminescent Biosensors of this invention provide an accurate, precise, sensitive, and reliable means for the determination of ethanol and other important chemical species in, for example, Closed Loop Regenerative Life Support System aqueous streams. Operation of the sensors is based upon the oxidation of the target compound (analyte), producing hydrogen peroxide ($H_2O_2$), which then reacts with luminol (a luminophore) to produce light. The intensity of the light is directly proportional to the concentration of the target compound. Advantages inherent to the technique are the potential for detection of extremely low levels, the stability of the devices used to measure light intensity (photomultiplier tubes), and the use of solid state modules for the controlled release of reagents.

DETAILED DESCRIPTION OF THE INVENTION

Figure 1A:
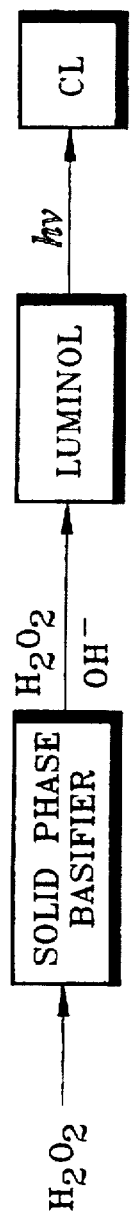
FIG. 1a is a block diagram of a detection scheme for hydrogen peroxide with a fiber optic chemiluminescent biosensor according to the present invention.
Figure 1B:
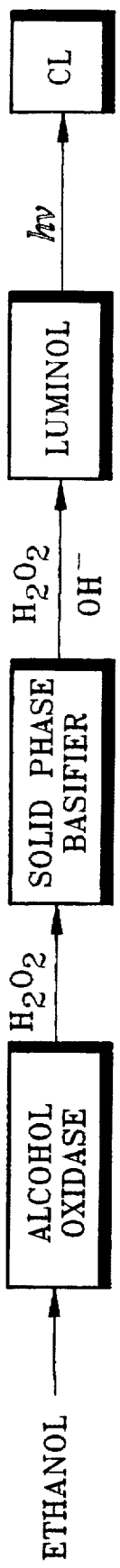
FIG. 1b is a block diagram of a detection scheme for ethanol with a fiber optic chemiluminescent biosensor according to the present invention.
Figure 1C:
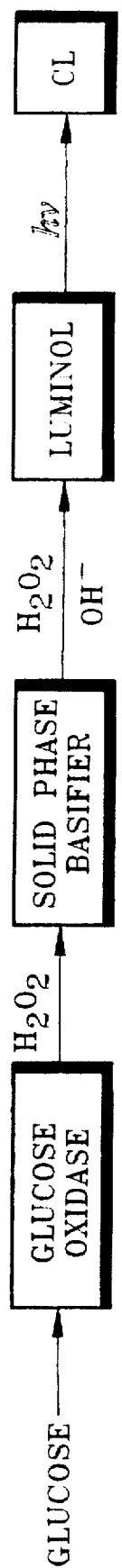
FIG. 1c is a block diagram of a detection scheme for D-glucose with a fiber optic chemiluminescent biosensor according to the present invention.

For clarity and convenience, the invention is discussed below in the context of three exemplary target species: ethanol, glucose, and hydrogen peroxide. These compounds demonstrate the use of the present chemiluminescent sensors across a diverse range of applications. Ethanol is an extremely important aqueous contaminant because it is poorly removed by physicochemical processes such as multifiltration and reverse osmosis, and consequently forms a significant fraction of the effluent total organic carbon (TOC) for these processes. Glucose is important from a biomedical standpoint. This simple sugar can play an important role as an essential carbon source for fermentation bioreactors, and as the product of biological processes for the decomposition of inedible plant biomass. $H_2O_2$ can find application as a surface disinfectant, as a means for the control of microbial populations in plant growth nutrient delivery systems, and as an oxidant for the decomposition of solid wastes and aqueous organics. The detection schemes for each of these target species is illustrated in FIGS. 1a–1c.

The simplest of the three sensor systems is that for detecting $H_2O_2$. The $H_2O_2$ containing aqueous stream flows through a solid phase basification module where the pH is adjusted to 10 by the reaction of equation (1):

$$MgO + H_2O \rightarrow Mg^{++} + 2OH^- \quad (1)$$

The basified effluent flows into a bed of luminol crystals which slowly dissolve at a controlled rate. The solution then flows into an Electrocatalyzed Luminescence (ECL) cell. A controlled voltage across the anode and cathode catalyzes the oxidation of luminol by $H_2O_2$. Light is emitted as a by-product of the reaction. The light is detected and quantified by a photomultiplier tube (PMT). The intensity of the light emission is directly proportional to the $H_2O_2$ concentration in the sample stream. The reaction of $H_2O_2$ with luminol is summarized in equation (2):

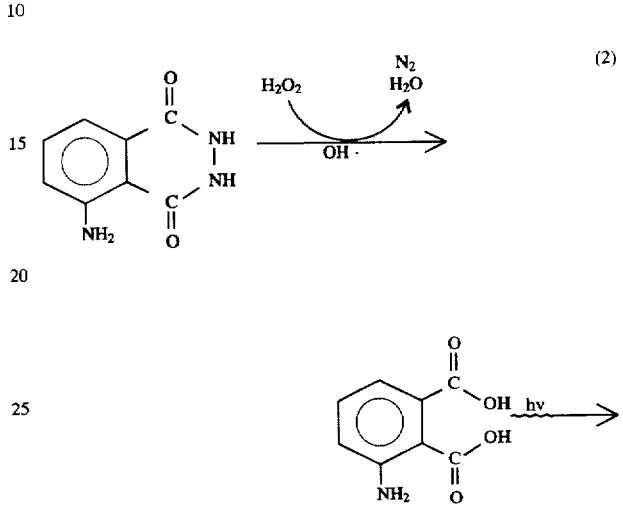

(2)

This simple detection scheme is extended to other target compounds through the use of immobilized enzymes. Ethanol is detected using the enzyme alcohol oxidase. Alcohol oxidase catalyzes the reaction of ethanol with molecular oxygen to form acetaldehyde and $H_2O_2$.

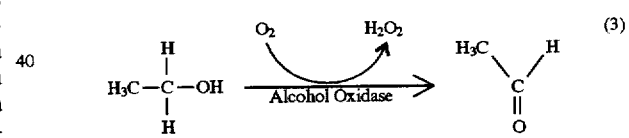

(3)

The $H_2O_2$ formed in this way is then basified, mixed with luminol and quantified by chemiluminescence in the ECL cell, as with the $H_2O_2$ sensor. Glucose is a six carbon sugar which, in aqueous solution, occurs in a hemiacetal pyranose ring structure. Glucopyranose occurs in two anomeric forms, termed α and β, which differ as to the position of the hydroxl group at the number 1 carbon position. The two are interconverted via the acyclic aldose intermediate as shown in equation (4). The two anomers occur in the ratio of 2:1, with the β anomer occurring in largest number. The glucose oxidase enzyme catalyzes the oxidation of β-D-glucopyranose to D-glucono-δ-lactone by molecular oxygen as shown in equation (5). $H_2O_2$ is also produced on a 1:1 molar basis as a by-product of the reaction.

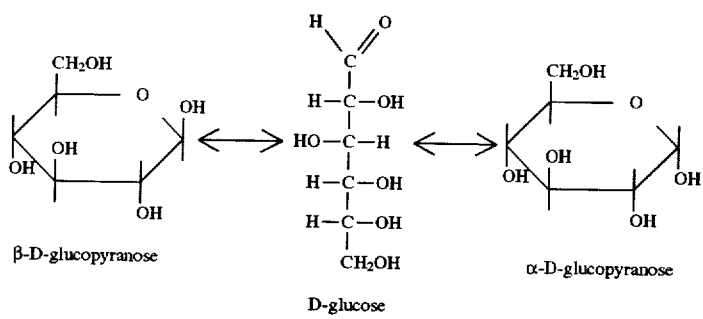
(4)

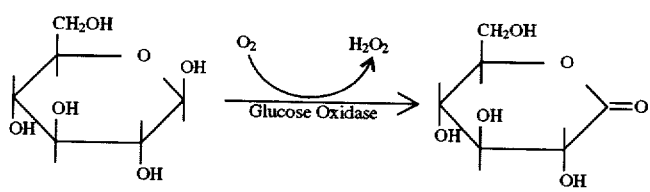
(5)

The H₂O₂ produced in the oxidation of glucose is then detected "reagentlessly" as outlined above, by flowing sequentially through a solid phase basification bed, a solid phase luminol bed, and the ECL detection cell.

Oxidation-reduction reactions catalyzed by enzymes require co-factors such as nicotinamide adenine dinucleotide (NAD), nicotinamide adenine dinucleotide phosphate (NADP), or flavine adenine dinucleotide (FAD). These co-factors are oxidized or reduced as part of the enzymatic reactions and must be either regenerated or introduced as a reagent for sustained biosensor performance. The oxidase family of enzymes offers the unique advantage of having the FAD co-factor incorporated into the enzyme structure, and in having the FAD regenerated as a consequence of the overall reaction.

The basic detection and quantitation technique outlined above for ethanol and glucose can be adapted to the determination of other compounds for which the respective oxidase enzymes are available. Examples of other compounds which are amenable to these methods are lactic acid (lactic acid oxidase), amino acids (amino acid oxidase), glutamic acid (glutamate oxidase), lysine (lysine oxidase), oxalic acid (oxalate oxidase), phenols (polyphenol oxidase), cholesterol (cholesterol oxidase), hypoxanthine (xanthine oxidase), L-α-glycerol phosphate (L-α-glycerol phosphate oxidase), choline (choline oxidase), ascorbic acid (ascorbate oxidase), and sulfite (sulfite oxidase). The reactions for lactic acid, alanine, phenol, and cholesterol are given below in equations (6)–(9), respectively:

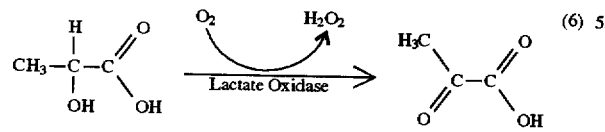
(6)

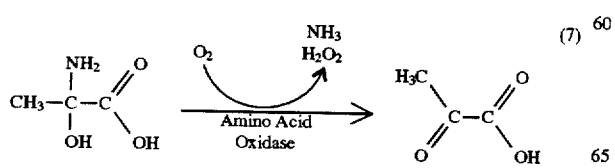
(7)

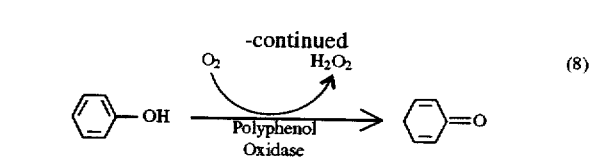
(8)

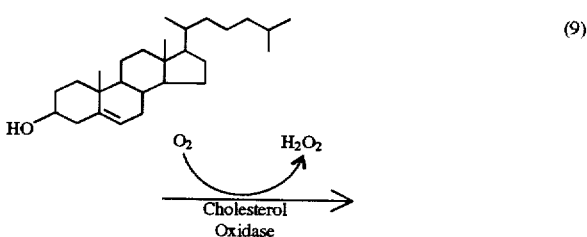
(9)

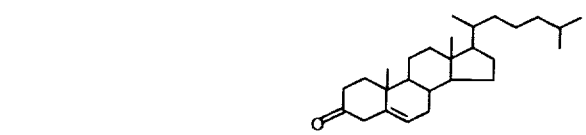

The chemiluminescence technique can also be applied to the detection of oxidizing agents other than H₂O₂. For example, elemental iodine (as HOI) can be quantified by the chemiluminescent reaction with luminol.

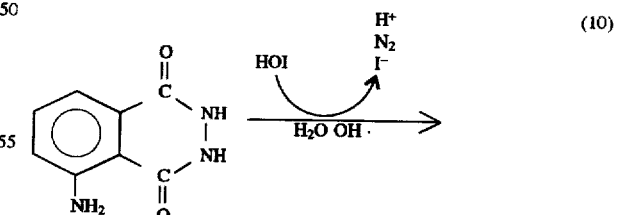
(10)

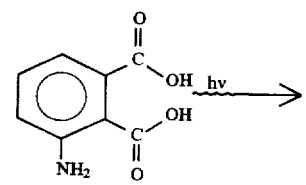

In the highly alkaline medium in which the reaction takes place, the hydrolytic disproportionation reaction of elemental iodine is strongly shifted toward the formation of HOI.

$$I_2 + H_2O \rightleftharpoons HOI + I^- + H^+ \quad (11)$$

Figure 2:
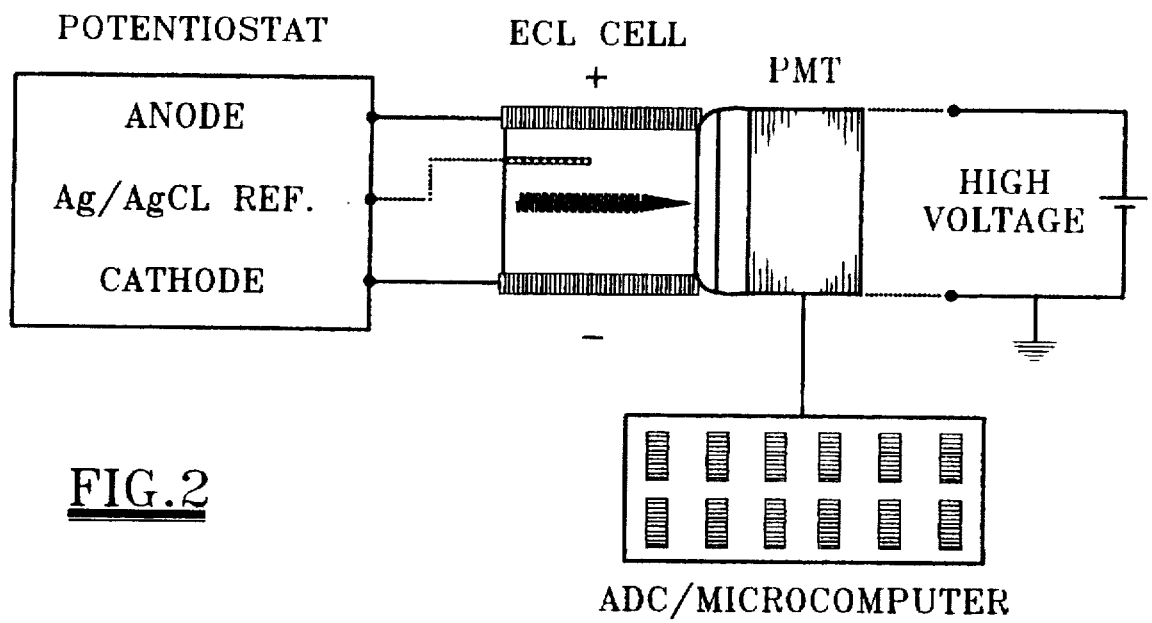
FIG. 2 is a schematic diagram of electrocatalyzed luminescence according to the present invention.

The light emitted during the chemiluminescence reaction is detected and measured using a photomultiplier tube (PMT). By using an electrical potential across the ECL cell to catalyze the reaction of hydrogen peroxide with luminol, the reaction is confined spatially, since the excited metastable state of the reaction product has a short half-life. Light can be gathered efficiently by coupling the PMT directly to the ECL cell, or by using fiber optics as a waveguide to carry the light to a remotely located PMT. The 43 essential features of an ECL cell with integral PMT are illustrated in FIG. 2.

The ECL apparatus comprises a three electrode electrolytic cell. A potentiostat is used to maintain the desired potentials at the working (anode) and counter (cathode) electrodes versus a Ag/AgCl reference. In FIG. 2, an end-on PMT is optically coupled to the cell. In operation, chemiluminescent light passes through a transparent face of the ECL cell and strikes the photocathode of the PMT. By the photoelectric effect, electrons are dislodged from the photocathode and accelerated by a high voltage field toward the first PMT dynode. PMTs operate by dividing a high voltage in the range of 1,000–1,500 V across a series of 10–12 dynodes. At each dynode, electrons collide with the surface and dislodge a greater number of electrons, which are accelerated toward the next dynode by the electric field. Each dynode multiples the number of electrons associated with the original light detection event. The numbers of electrons are thus amplified in a cascading effect from dynode to dynode. Overall PMT gains of $10^6$ are typical. One photon detected results in a current of one million electrons. This feature gives the chemiluminescence biosensors extreme sensitivity.

EXAMPLES

Sensors for ethanol, glucose, and hydrogen peroxide were investigated. Sensors for each of these species were successfully demonstrated. Ethanol (as C) was detected in the concentration range 40–4,000 µg/L (ppb). Given the relatively crude system used in these examples, it is believed that a breadboard ethanol sensor can obtain detection limits in the range of 1–5 µg/L.

Chemicals

Alcohol oxidase (alcohol oxygen oxidoreductase, EC 1.1.3.13) was purchased from Provesta (Bartlesville, Okla.). Glucose oxidase (glucose oxygen oxidoreductase, EC 1.1.3.4), acetic acid, and ethylene diamine were purchased from Sigma (St. Louis). Luminol (3-aminophthalhydrazide), 3-aminopropyltriethoxysilane, D-glucose, glutaric dialdehyde (glutaraldehyde), sodium tetraborate decahydrate, hydrochloric acid, dibasic sodium phosphate, monobasic potassium phosphate, sodium acetate, 30% aqueous hydrogen peroxide, and ethanol were purchased from EM Science. Dimethyl sulfoxide and copper sulfate were purchased from VWR Scientific (Portland).

Supports

Celite Bio-Catalyst Carrier R-648 (diatomaceous earth) was purchased from Manville (Denver). Porosil C, controlled porosity glass (CPG) beads with 20–40 nm pore size and 50–100 m²/g surface area was purchased from Alltech (San Jose).

Apparatus

Spectra were acquired using a Hewlett-Packard 8452A diode array spectrophotometer. Electrode potentials were controlled using a Pine Instrument Company model AFRDE potentiostat. Light detection was achieved using a ten dynode Hamamatsu R878 5.08 cm (2") diameter head-on type photomultiplier tube (PMT) with optimal spectral response at 420 nm, and a Nucleus TB-1 photomultiplier tube base. High voltage was applied to the PMT using a Nucleus model 575 scaler-ratemeter power supply. Conditioned PMT output was monitored using a Linear model 2030 chart recorder. In-line pH was determined using Cole Parmer 05992-64 flow through pH electrodes. Flows were established using Masterflex model 7520-35 multichannel peristaltic pumps. Electrocatalyzed chemiluminescence cells were constructed using a Bioanalytical model 94332 gold mesh electrode, an Alfa model 14721 gold foil electrode, and a Microelectrodes model MI 402 Ag/AgCl reference microelectrode. Polarity switching frequencies were synthesized using a Wavetek model 142 function generator. The fiber optic waveguide was constructed from Edmund Scientific model N39,371 shielded glass fiber optic cable, consisting of 50,000 strands.

Example 1

Silane Linkage to CPG

Figure 3A:
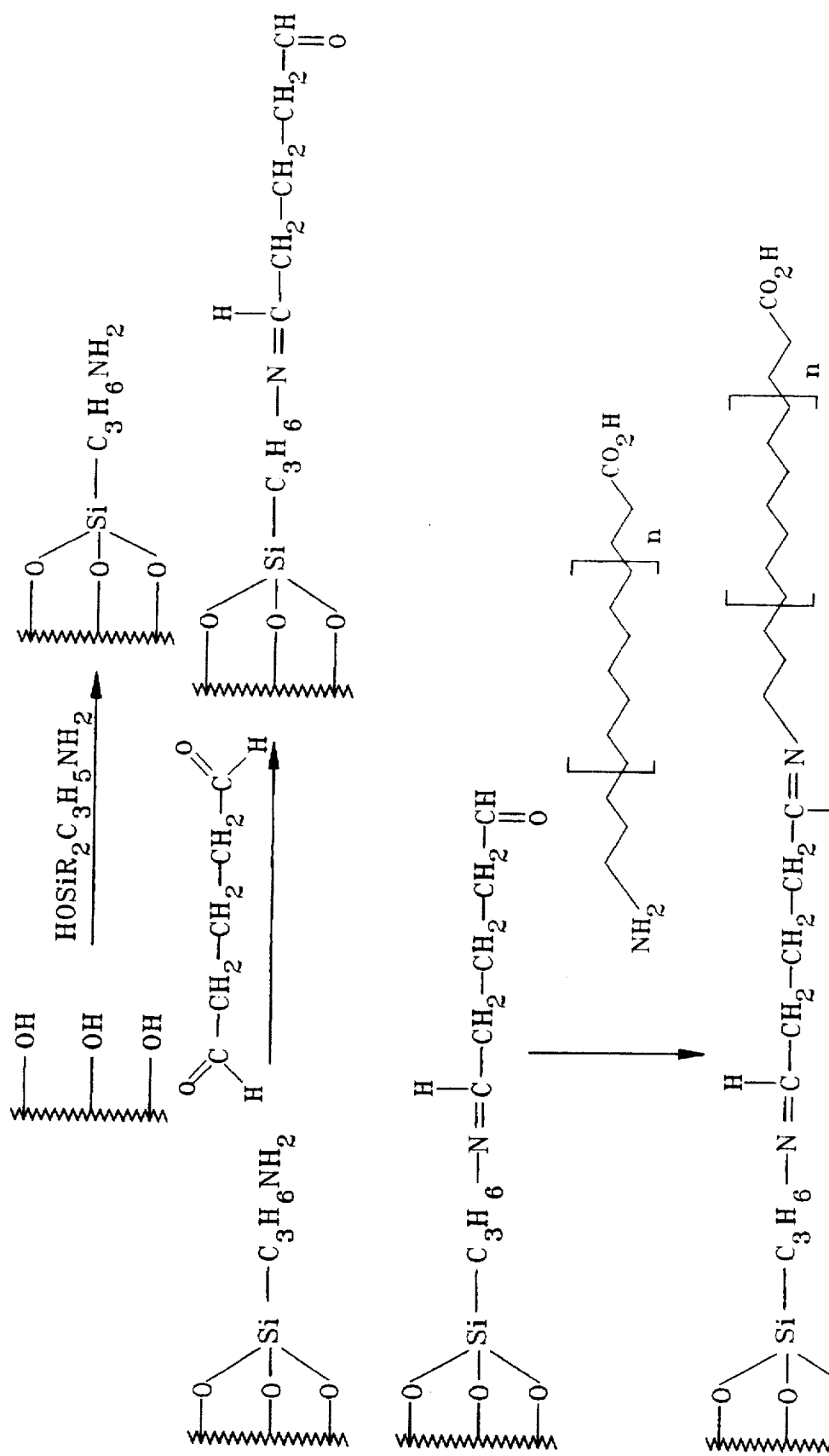
FIG. 3a shows the chemical reactions involved in enzyme immobilization by silane linkage to controlled porosity glass (CPG).

Glucose oxidase and alcohol oxidase were immobilized on controlled porosity glass (CPG) beads as summarized in FIG. 3a. Five grams of CPG beads were placed in 250 mL of 0.05M acetate buffer (pH=5) prepared from acetic acid and sodium acetate. The solution was boiled on a stirred hot plate to remove gas and thoroughly wet the beads. Three mL of 3-aminopropyltriethoxysilane (APTES) were added when the solution had cooled to 90° C. The solution was stirred at this temperature for one hour. Under acidic conditions, the surface terminating oxygens on CPG are protonated. The hydroxyl groups reacted with APTES ethoxy groups, liberating ethanol, and forming silicon-oxygen-aminoalkylsilane linkages. The linked aminosilanes terminated in a free amine group. The reaction mixture was cooled and washed three times each with 50 mL portions of deionized (DI) water, ethanol, DI water, and phosphate buffer (pH=8.5) prepared from 0.05M solutions of dibasic sodium phosphate and monobasic potassium phosphate.

The silanized CPG beads were then added to 20 mL of 12% glutaraldehyde in phosphate buffer solution (pH=8.5) and stirred for 2 hours. The Schiff base reaction between one end of the dialdehyde and the free amino group of the silanized CPG formed an imine bond with an aldehyde terminus. At this stage, the CPG beads took on a reddish brown coloration. The beads were then rinsed three times each with 50 mL portions of phosphate buffer (pH=7.5) and DI water.

Either 50 mg of glucose oxidase in acetate buffer (pH=4) or 1.2 mL of alcohol oxidase in a buffered sucrose solution (1200 EU) were combined with one gram of derivatized CPG beads. This combination was rolled in a glass jar for 96 hours at room temperature, and then washed three times each with 50 mL portions of DI water and phosphate buffer (pH=7.5). This step completed the covalent linkage of the enzymes to CPG via another Schiff base reaction between free amino groups on the enzyme and the free aldehyde groups attached to the CPG beads. Immobilized enzymes were refrigerated in phosphate buffer solution at 4° C. until used.

Example 2
Luminol Immobilization on CPG

Figure 3B:
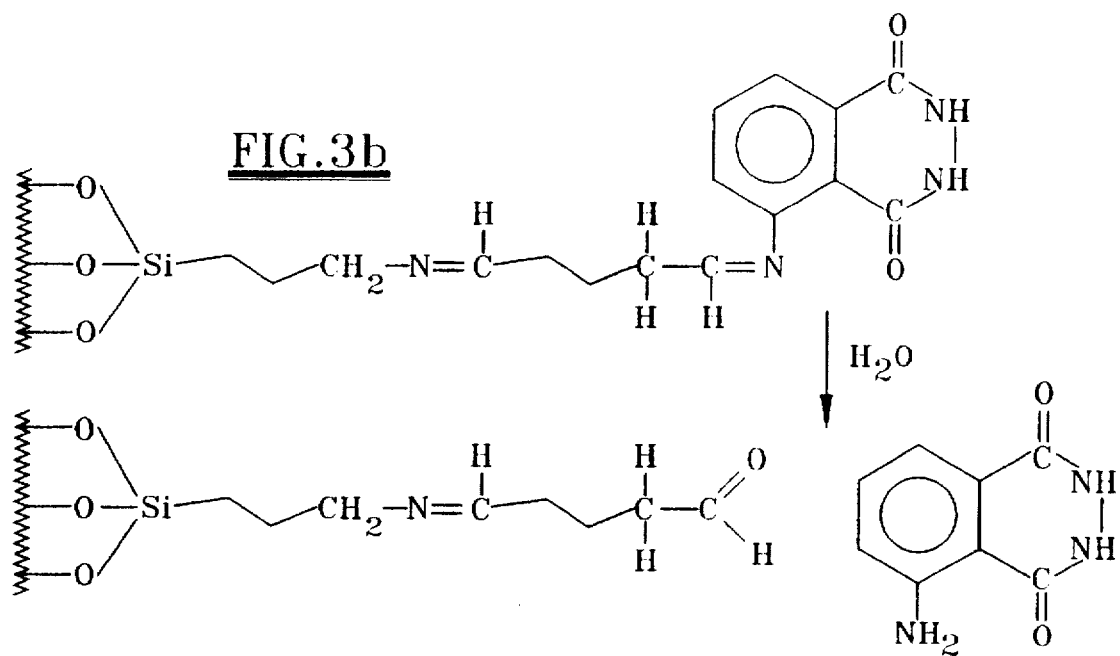
FIG. 3b shows the chemical reactions involved in luminol immobilization by silane linkage to controlled porosity glass.

Luminol was immobilized on CPG in a similar manner to that outlined above in Example 1, using the free amino group attached to the number 3 carbon. Luminol was dissolved in a 1:1 mixture of dimethyl sulfoxide and ethanol. A 125 mL aliquot of the luminol solution was added to 5 gm of silanized CPG beads which had been previously silanized and reacted with glutaraldehyde as in Example 1. The reaction mixture was stirred at room temperature for 15 hours. After completion of the reaction, the CPG beads were washed five times each with 100 mL portions of ethanol followed by DI water. The CPG immobilized luminol was stored in deionized water until used. As illustrated in FIG. 3b, luminol immobilized in this manner is released to the aqueous solution by slow hydrolysis reactions.

Example 3
Titanium Linkage to Diatomaceous Earth Support (DES)

Figure 4:
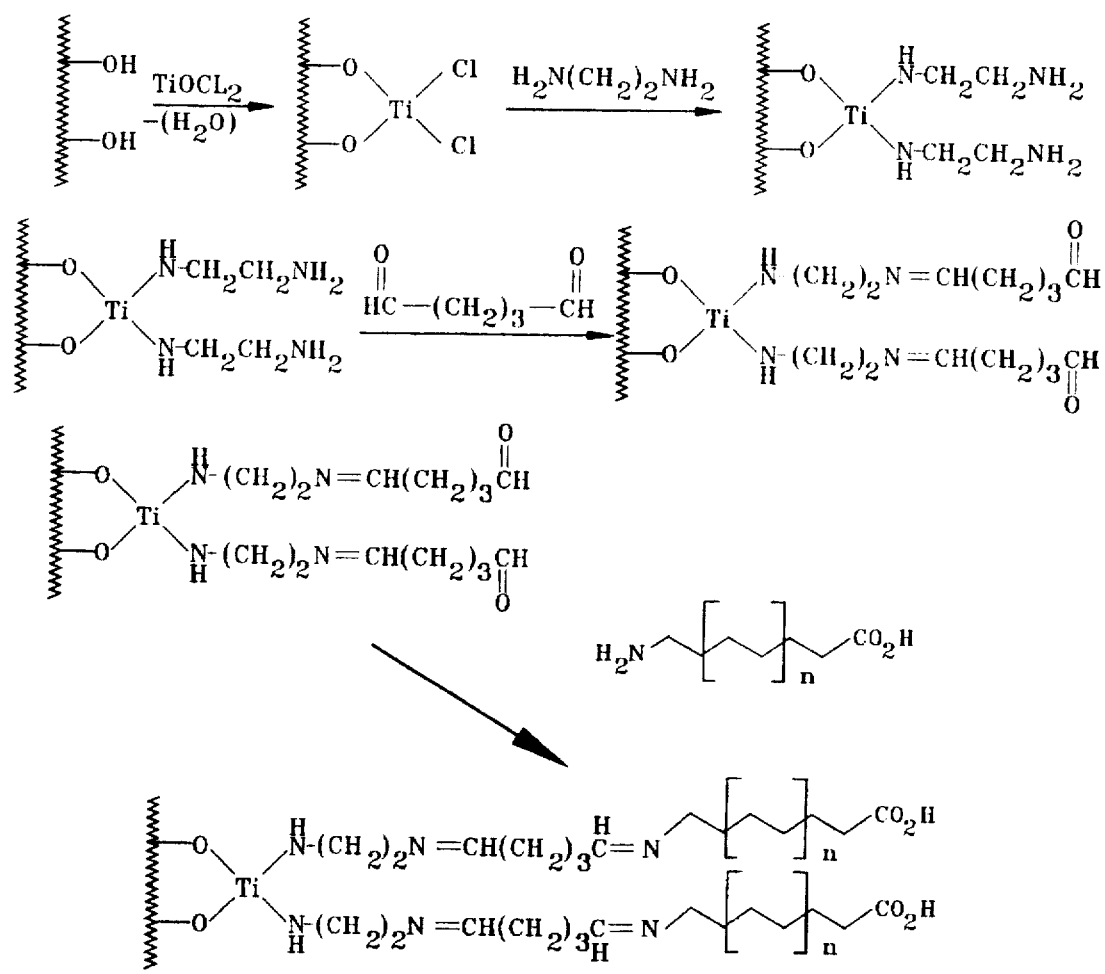
FIG. 4 shows the chemical reactions involved in enzyme immobilization by titanium linkage to diatomaceous earth.

Glucose oxidase and alcohol oxidase were immobilized on DES as summarized in FIG. 4. A 15% solution of titanium oxychloride ($TiOCl_2$) was prepared by slowly dropping titanium tetrachloride into a 10% hydrochloric acid solution maintained in an icebath at 5° C. This solution was refrigerated until used. A 40 g portion of R-648 DES was added to 100 mL of 15% $TiOCl_2$ solution. The solution was then evaporated to dryness under vacuum at 45° C. The HCl containing exhaust gases were trapped by a sodium bicarbonate solution. This reaction formed a silicon-titanium bond and left two chlorines attached to the titanium. The dried activated support was washed four times with 100 mL portions of methanol, until the yellow residual color disappeared, and then dried overnight at room temperature.

A 40 g portion of activated support was combined with 100 mL of 5% ethylene diamine in carbon tetrachloride, and then heated in an oven at 45° C. for two hours. The DES was then washed twice each with 100 mL portions of methanol followed by DI water. In this reaction, the free amino groups of ethylene diamine formed Ti-N linkages to the surface bonded titanium and displaced the surface bonded chlorine. The second amine remained free for the subsequent Schiff base reaction. A 125 mL aliquot of 5% glutaraldehyde in phosphate buffer (pH=8.5) was added to the DES. The resulting suspension was rolled overnight. This reaction created a diazo linkage between between the DES surface and one of the free aldehyde groups from the dialdehyde. At this stage, coloration of the activated support turned a darker shade of brown. The DES was then washed five times with 200 mL portions of DI water, and dried at room temperature.

A 12,000 EU portion of phosphate buffered alcohol oxidase in sucrose solution (or 10,000 EU of glucose oxidase in an acetate buffer solution (pH=4) was added to 10 g of derivatized support in 20 mL of acetate buffer (pH=4). The mixtures were rolled for 96 hours at room temperature. A Schiff base reaction between free amino groups of the enzyme and the tethered aldehyde bound the enzymes covalently to the DES. The enzyme coated support was washed with DI water until the specific conductance of the wash solution was less than 1 µS/cm. The immobilized enzymes were stored in phosphate buffer (pH=7.5).

Example 4
Solid Phase Basification Beds

Two solid phase basification (SPB) materials were examined as candidates for the flow through pH conditioning bed. These were $CaCO_3$ and MgO. Due to the high pH required for efficient chemiluminescence (pH=10–11), MgO was selected for use in the fiber optic chemiluminescence biosensor due to its higher equilibrium pH response. The crystalline material was ground up and sieved, forming four groups of varying particle size (75–106, 150–300, 300–600, and 600–1000 µm). Samples representing each of these size distributions were then loaded into small columns with a total volume of 1.4 mL. DI water was pumped through the columns at varying flow rates. Effluent pH versus empty bed contact time was determined for each of these size ranges.

Example 5
Electronic Circuits

Figure 5:
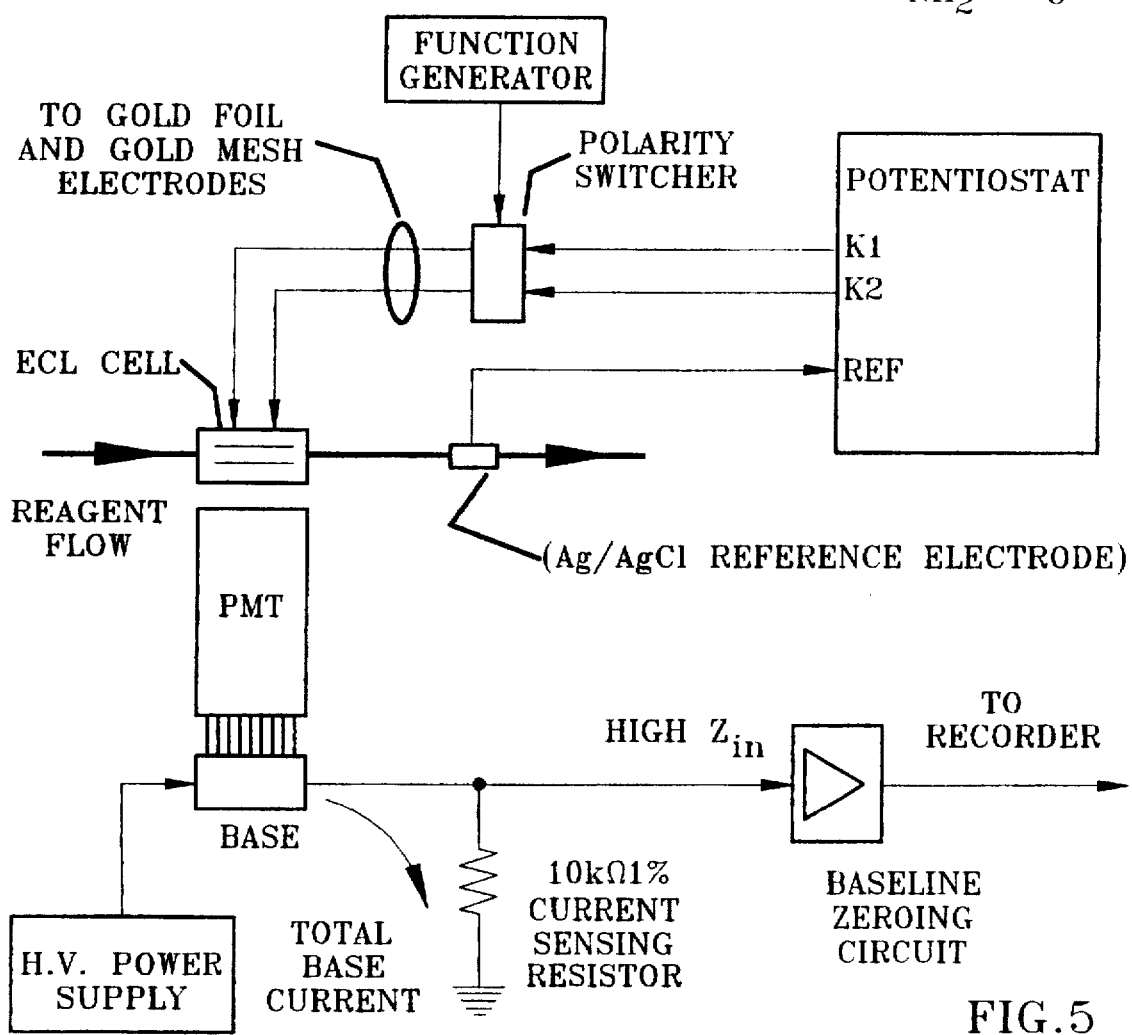
FIG. 5 is a schematic illustration of an electrocatalyzed chemiluminescence detection system according to the present invention.

An electrocatalyzed chemiluminescence detection system was constructed with the system electronics shown in FIG. 5. The photomultiplier tube received a positive bias of 1,280 V from the high voltage power supply. The current through the PMT Base, which was proportional to light intensity, was input to the Baseline Zeroing Circuit in the form of a voltage drop across a 10 kΩ 1% current sensing resistor. A baseline corrected voltage was then output to the strip chart recorder.

Figure 6:
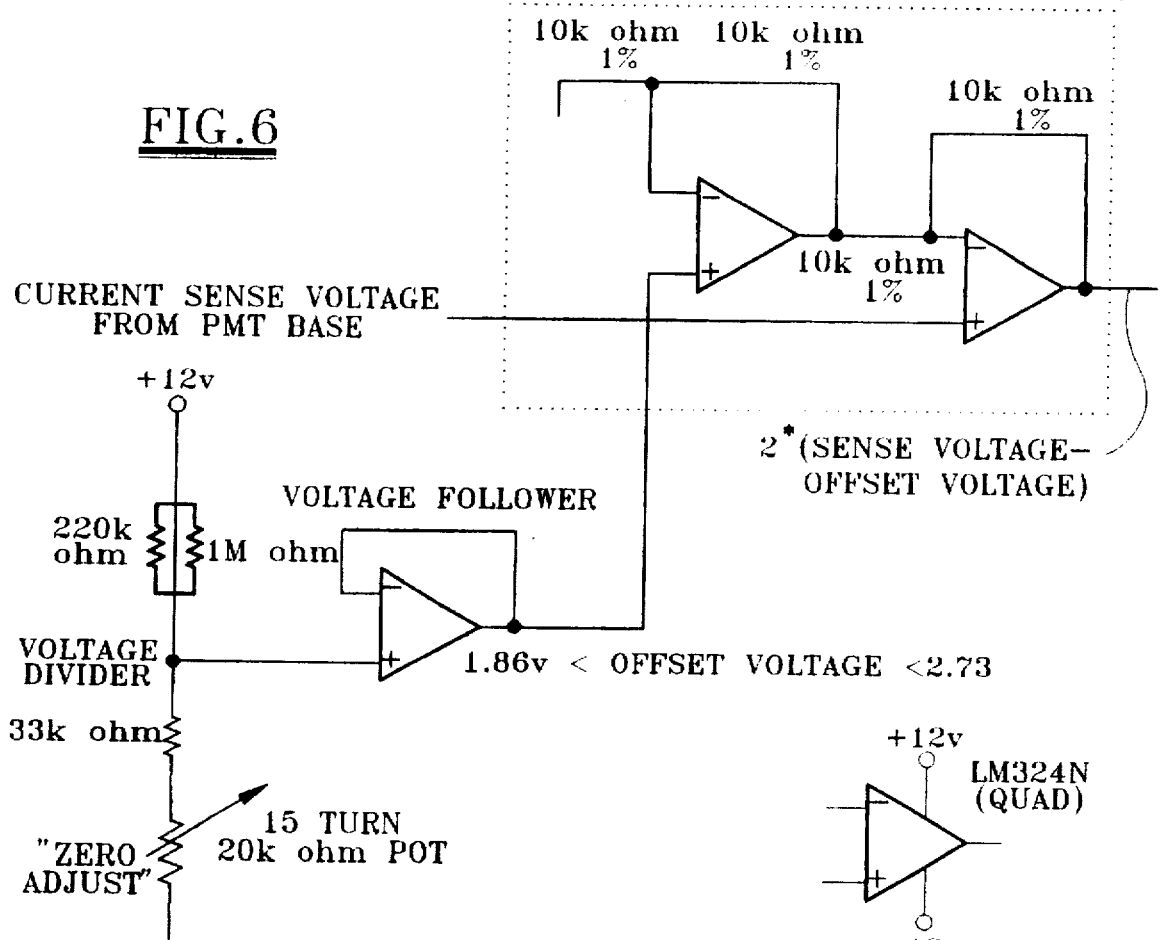
FIG. 6 illustrates a base line zeroing differential amplification circuit used in the detection system of FIG. 5.

The PMT base was modified to provide a low voltage output across an external current sensing resistor. In order to provide a signal that was proportional to small increases in current through the PMT base, a Baseline-Zeroing Circuit was designed and constructed as shown in FIG. 6. A high input impedance DC Differential amplifier, built using LM324N operational amplifiers and 10 kΩ 1% resistors, was used to compare the signal to an adjustable offset voltage. The differential amplifier output was a voltage proportional to the difference between the input and the offset voltages. The offset voltage was supplied by a voltage divider network through a potential follower. A fifteen turn 20 kΩ potentiometer allowed the operator to reduce the voltage output, corresponding to the PMT dark current, to less than 1 mV. The differential amplifier also provided an overall gain of 2.

The chemiluminescent reaction was electrocatalyzed in the ECL cell by a potential of approximately 0.8V applied across a gold foil working electrode (anode) and a gold mesh counter electrode (cathode). Both voltages were maintained relative to a Ag/AgCl reference electrode by the potentiostat. Polarity switching of the electrodes was incorporated into ECL cell operation to prevent deterioration of performance due to formation of an oxide coating on the gold electrode surfaces. Under conditions of alternating polarity, each oxidation step was followed by a corresponding reduction. A polarity switcher circuit, driven by a function generator, was designed and constructed to provide this function.

Figure 7:
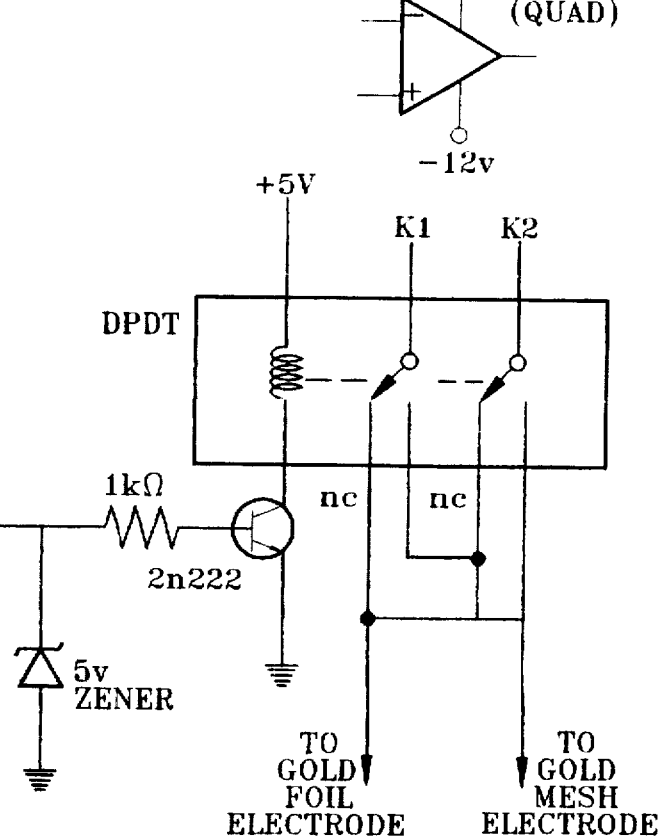
FIG. 7 illustrates a polarity switching circuit used in the detection system of FIG. 5.

The Polarity Switcher circuit is shown schematically in FIG. 7. Control current for an electromechanical DPDT relay was switched through a 2n222 transistor by the regulated periodic square wave output of the function generator. The K1 and K2 voltages from the potentiostat were each connected to a separate relay switch common. The normally closed and normally opened relay switch outputs were wired to provide polarity switching as a consequence of the relay being periodically energized and de-energized. The variable frequency of polarity switching was determined by the frequency selected for the function generator square wave output. This circuit was normally operated at frequencies less than 5 Hz.

Example 6
Chemically Catalyzed Chemiluminescence Cell

Two separate chemiluminescent cells were designed and fabricated for chemically and electrically catalyzed oxidation of luminol respectively.

Figure 8:
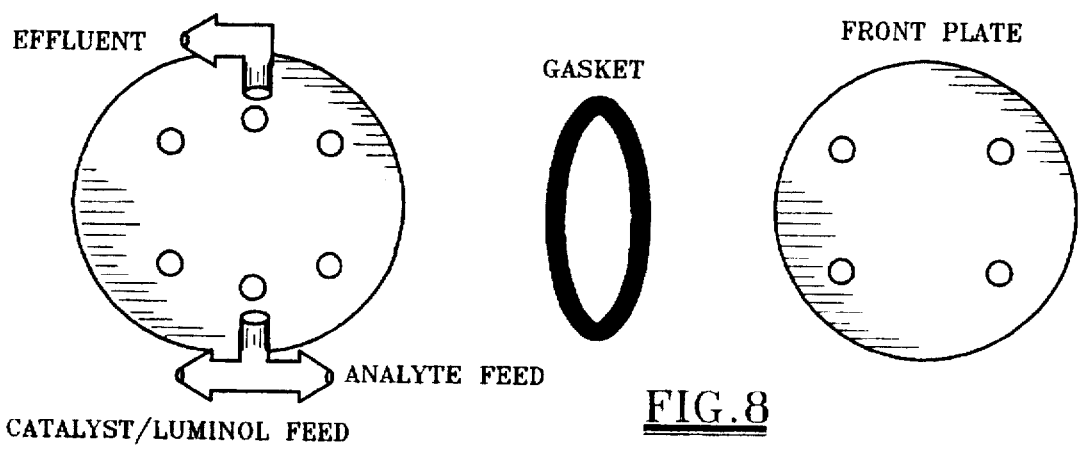
FIG. 8 is an exploded view of a chemically catalyzed chemiluminescence detection cell according to the present invention.

The chemically catalyzed luminescence detection cell is shown schematically in FIG. 8. This cell was constructed using two polycarbonate circular plates 0.48 cm (3/16") thick and 5.08 cm (2") in diameter, separated by a silicone O-ring. The PMT was optically coupled to the surface of the front plate. The internal volume of the cell was approximately 500 µL and the photoactive area was approximately 3 $cm^2$. In operation, a flowing stream containing basified luminol and $Cu^{+2}$ catalyst was combined with a separate target analyte containing stream at the inlet to the cell. Photons emitted from the solution were transmitted through the front plate of the cell and detected by the PMT.

Example 7
Electrocatalyzed Chemiluminescence Cell

The ECL cell is shown schematically in FIG. 8. The ECL cell was also constructed from two 0.48 cm (3/16") thick polycarbonate circular plates 5.08 cm (2") in diameter. Attached to the inside of the front plate was a 2.54 cm (1") square gold mesh electrode with a mesh density of 39 lines per cm, and a gold contact wire. The PMT was optically coupled to the external surface of the front plate. A 25 mm square of 1 mm thick gold foil electrode with gold contact wire was attached to the inside of the back plate. A 0.038 cm (0.015") thick Teflon® gasket with a tortuous flow path was used as a spacer to separate the plates. The tortuous path configuration was found to improve overall performance by ensuring that air bubbles were not trapped within the cell. The ECL cell functioned by combining flowing streams of target analyte and basified luminol at the influent orifice and electrically catalyzing the luminol oxidation reaction within the cell. By maintaining a potential across the electrodes, photons were emitted from the flowing solution, some of which were transmitted through the gold mesh to the PMT.

Figure 9:
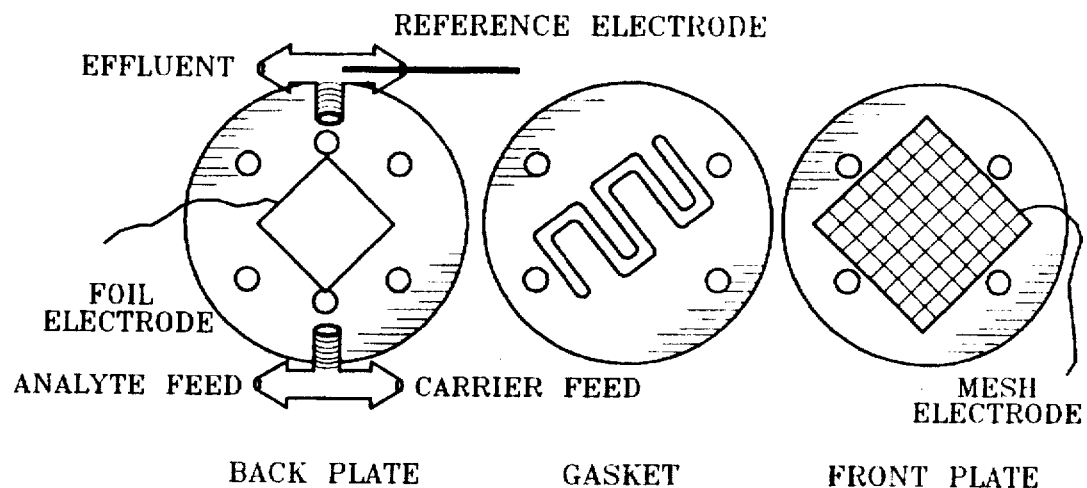
FIG. 9 is an exploded view of an electrocatalyzed chemiluminescence (ECL) cell according to the present invention.

Example 8
Integrated Chemically Catalyzed Chemiluminescent Biosensor Test Stand Preliminary experiments were conducted using chemically catalyzed chemiluminescence detection of hydrogen peroxide. These experiments were performed using the test stand illustrated in FIG. 9. A peristaltic pump was used to feed the chemically catalyzed chemiluminescent cell with three flowing liquid streams. The alkaline luminol stream was prepared by sequential flow of DI water through a MgO bed, a solid phase luminol bed, and a second MgO bed. The catalyst stream consisted of a 0.024 mM copper sulfate in DI water. These two streams were combined to form the carrier stream. The third stream, the analyte stream, was mixed with the carrier stream immediately prior to entry into the chemiluminescence detection cell. The analyte stream consisted variously of deionized water blanks and samples with differing levels of hydrogen peroxide dissolved in deionized water. Flow ratios of 1:1 were used for the carrier and analytical streams.

Figure 10:
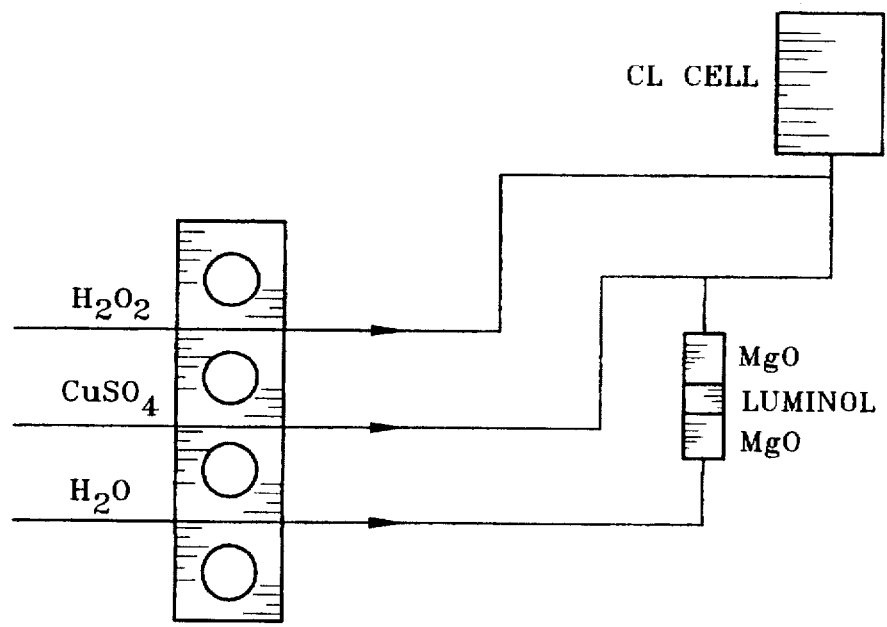
FIG. 10 is a schematic diagram of a chemically catalyzed chemiluminescent sensor test stand for detecting hydrogen peroxide according to the present invention.
Figure 11:
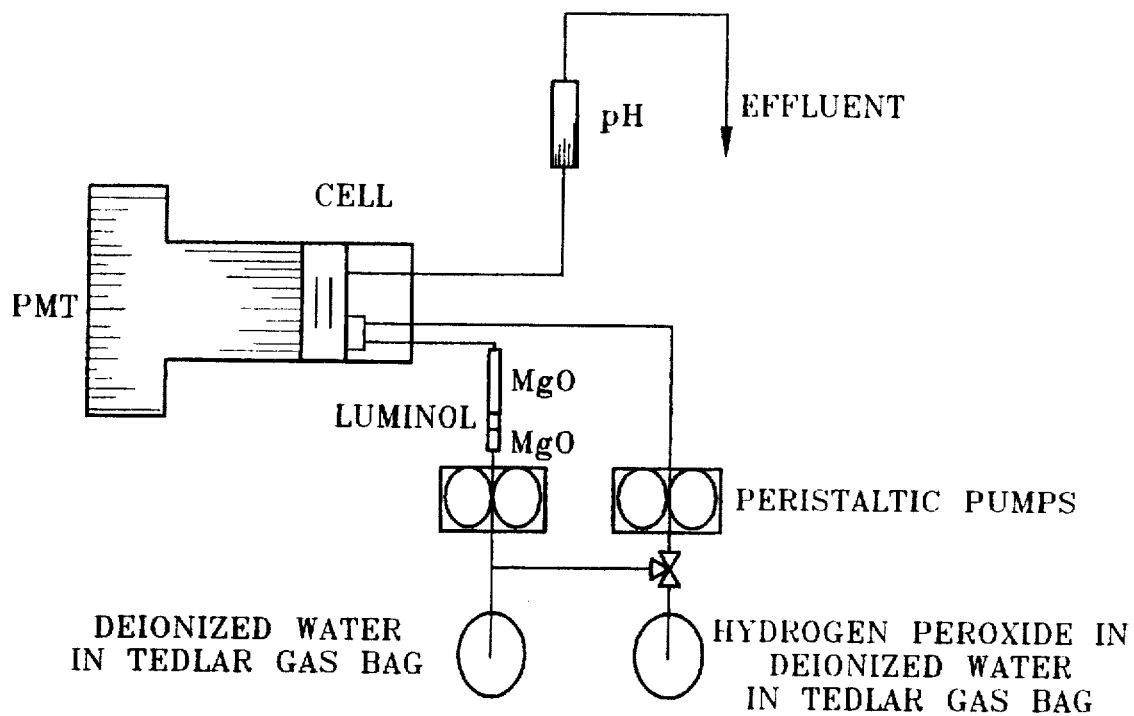
FIG. 11 is a schematic diagram of an integrated ECL chemiluminescent sensor test stand for detecting hydrogen peroxide according to the present invention.

Example 9
Integrated Electrically Catalyzed Chemiluminescent Biosensor Test Stand The integrated test stands fabricated for the electrically catalyzed detection of hydrogen peroxide, ethanol, and glucose differed slightly in their design and operation. FIG. 10 illustrates the integrated test stand for hydrogen peroxide detection and quantification. Independently controlled peristaltic pumps were used to establish carrier stream and analyte stream delivery to the electrocatalyzed luminescent (ECL) cell. The carrier stream consisted of degassed deionized water which had passed sequentially through a 2.5 $cm^3$ SPB bed, a 0.5 $cm^3$ crystallized luminol bed and a 5.0 $cm^3$ SPB bed. The resultant carrier stream contained 50 mg/L luminol at pH 10.3. The analytical stream consisted of varying levels of hydrogen peroxide in degassed deionized water. The carrier stream and the analytical stream were mixed inside the ECL cell.

Samples were analyzed by operating the carrier and analyte pumps for ten minutes prior to application of potential to the electrodes. After this equilibration period, a 0.8 volt potential difference, relative to the Ag/AgCl reference electrode, was applied between the gold foil anode and the gold mesh cathode for a period of one minute. A voltage peak from the PMT circuit proportional to the $H_2O_2$ concentration in the analytical stream was measured relative to baseline.

Example 10
Remote PMT

Figure 12:
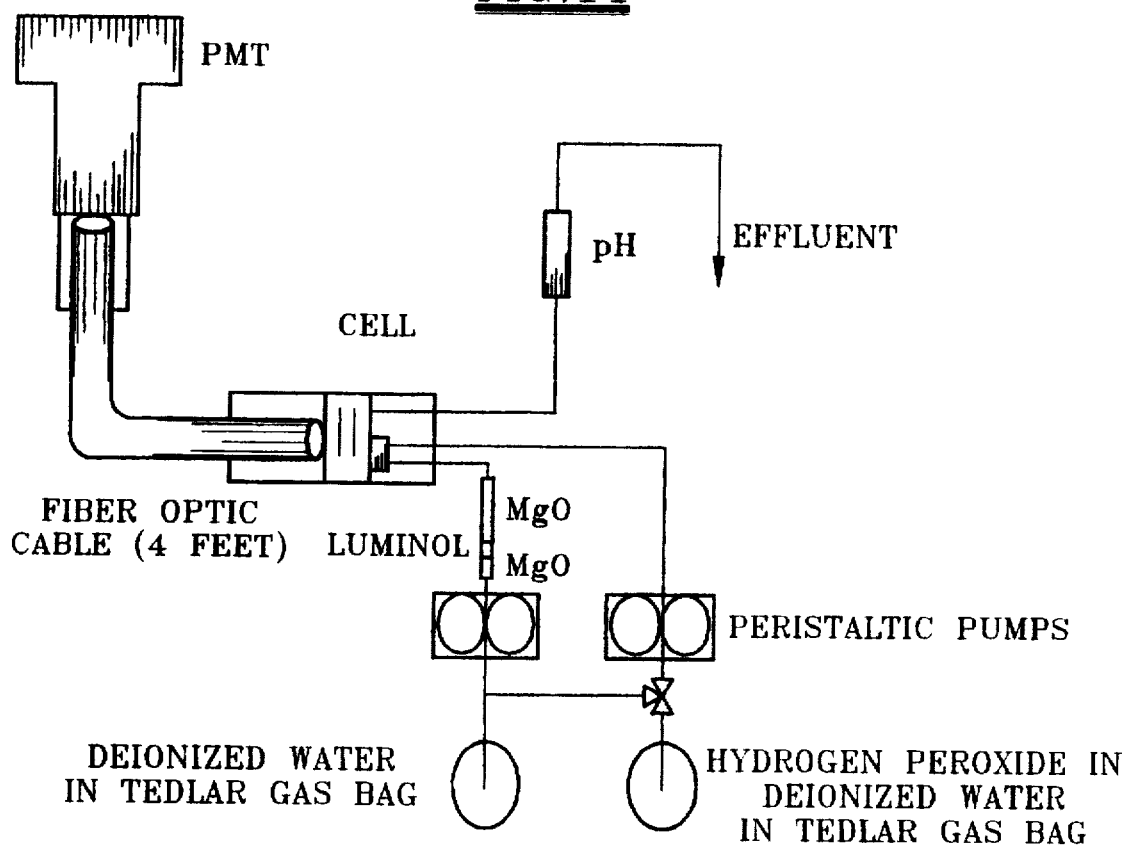
FIG. 12 is a schematic diagram of an integrated fiber optic chemiluminescent sensor test stand for the detection of hydrogen peroxide according to the present invention.

A test stand similar to that of Example 9 was constructed, except that light was transmitted from the ECL cell to a remotely located PMT via a four feet section of 50,000 strand shielded fiber optic cable, as shown in FIG. 12.

Examples 11 and 12
Ethanol and Glucose Defection Test Stands

Figure 13:
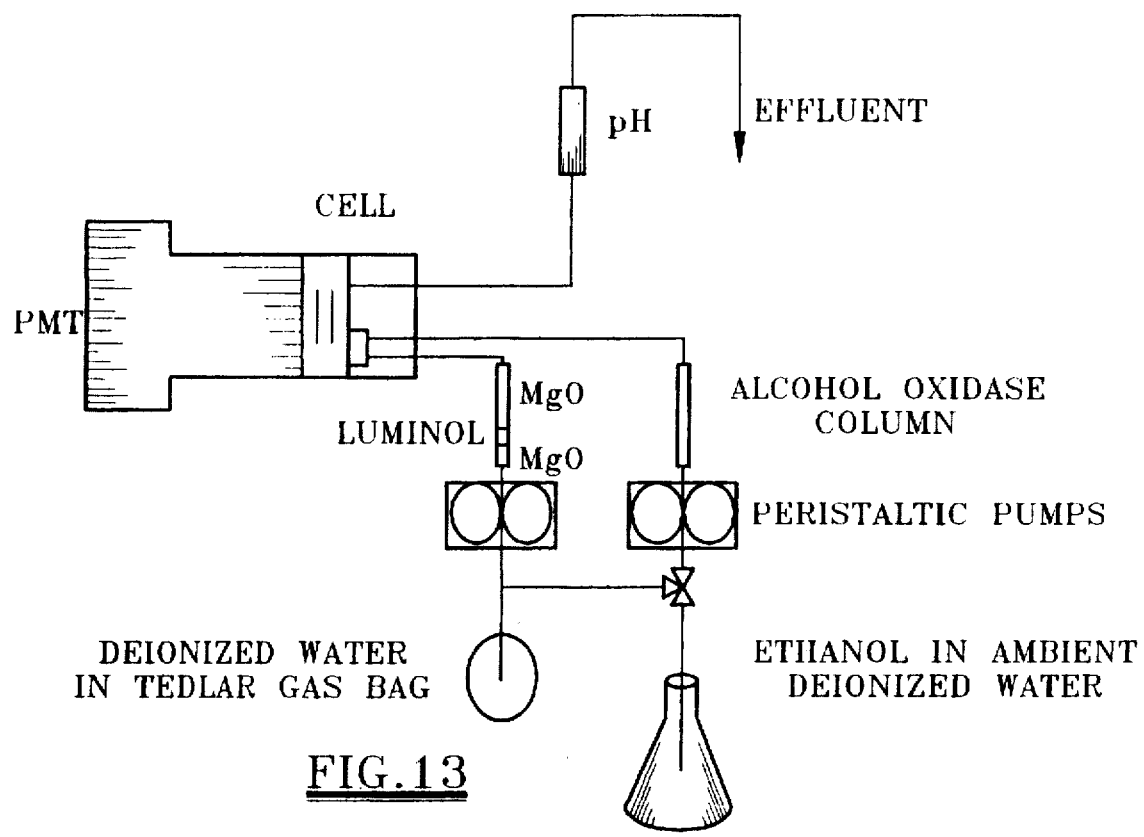
FIG. 13 is a schematic diagram of an integrated ECL chemiluminescent sensor test stand for the detection of ethanol according to the present invention.
Figure 14:
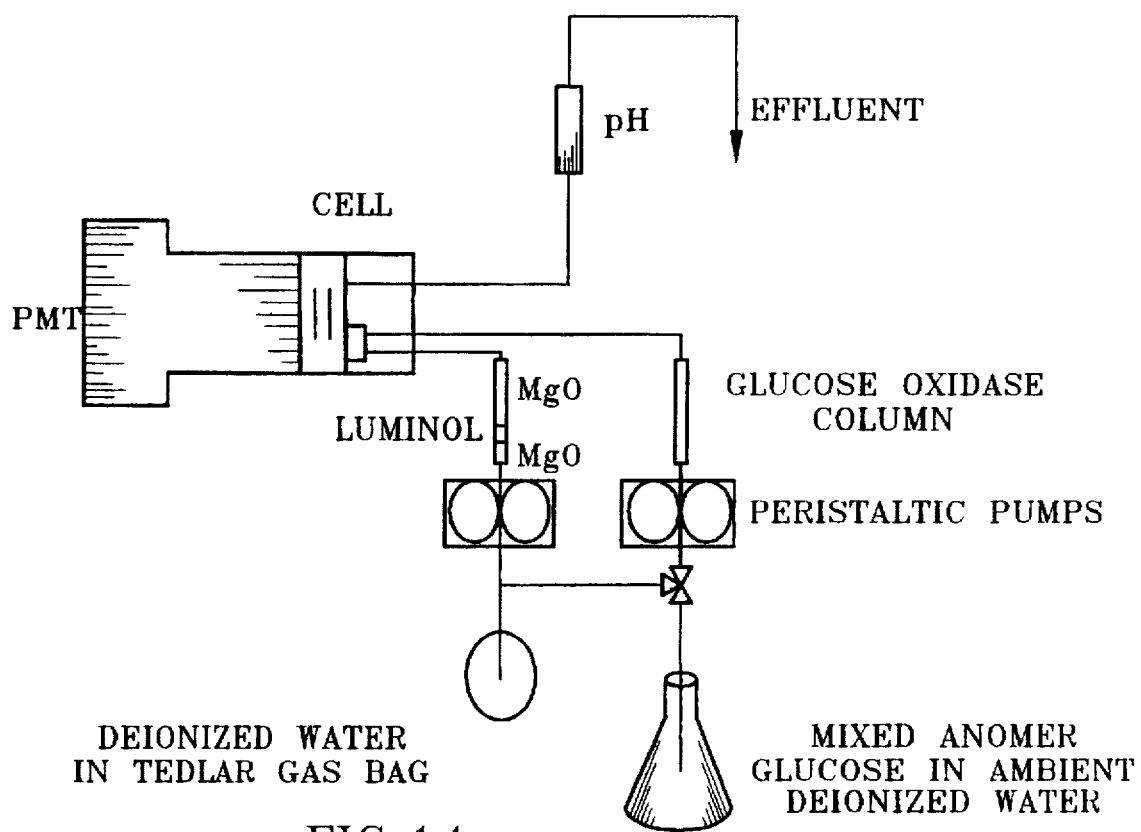
FIG. 14 is a schematic diagram of an integrated ECL chemiluminescent sensor test stand for the detection of D-glucose according to the present invention.

Integrated test stands for the determination of ethanol and glucose were shown in FIGS. 12 and 13, respectively. These differed from the systems of Examples 8–10 by the addition of the appropriate immobilized enzyme bed in the flow path of the analytical stream, and in the use of a borosilicate glass flask to contain the sample solution, rather than a Tedlar bag. For the ethanol sensor system, a 1.2 $cm^3$ bed of alcohol oxidase immobilized on DES was used. For glucose, a 2.7 $cm^3$ bed of glucose oxidase immobilized on CPG was used. The carrier to analytical stream flow ratios were 1:1, 1.5:1, and 11.7:1 for hydrogen peroxide, ethanol, and glucose determinations, respectively.

Each of the unit operations required for fiber optic chemiluminescent biosensor detection of hydrogen peroxide, ethanol, and glucose were investigated sequentially. These unit operations included: enzyme catalyzed substrate (ethanol and glucose) oxidation to produce $H_2O_2$, solid phase basification of the flowing aqueous stream to pH≈10, controlled release of luminol (the luminophore) into the aqueous stream, electrical catalysis of chemiluminescence, fiber optic light transmission of chemiluminescent emissions, and quantification of chemiluminescent light intensity. Enzyme immobilization procedures and $H_2O_2$ production rates for alcohol oxidase and glucose oxidase were investigated sufficiently to demonstrate production of $H_2O_2$ proportional to influent ethanol and D-glucose levels, respectively. Solid phase basification beds containing MgO were sized to consistently produce a consistently alkaline effluent. Solid phase modules for the controlled release of luminophore were investigated. Beds consisting of luminol chemically immobilized on glass beads and beds of crystalline luminol were studied. The latter required development of methods for luminol crystal growth. Preliminary investigations were conducted using chemically catalyzed chemiluminescence. Several designs for electrocatalyzed luminescence cells were evaluated. Operational electrode potentials and means for polarity switching required for stable detection and quantification of $H_2O_2$ were studied. PMT high voltage bias and detection circuit requirements were evaluated. This was followed by fabrication and testing of fully integrated chemiluminescent sensor systems for ethanol, $H_2O_2$, and glucose. Utility of the sensor systems was ultimately demonstrated by the development of calibration curves for $H_2O_2$, ethanol, and glucose. The utility of transmission of the chemiluminescence signal to a remotely located PMT via fiber optics was demonstrated by the development of a calibration curve for $H_2O_2$ using this technique.

Prior to assembly and testing of the integrated hydrogen peroxide, glucose, and ethanol chemiluminescent biosensors, each unit operation required for sensor performance was refined to ensure successful operation. These unit operations included: 1) solid phase basification of DI water to provide an effluent pH in the range of 10–11, using crystalline media in a packed flow-through bed; 2) controlled dissolution of a sufficiently high concentration of luminol in basified DI water using a flow-through module; 3) detection of luminescence; 4) electrocatalyzed chemiluminescent oxidation of luminol by hydrogen peroxide; and 5) enzyme catalyzed reaction of ethanol and glucose to produce hydrogen peroxide, using in-line beds of immobilized enzymes. Following the investigation and refinement of individual unit operations, the components were integrated into fully operational sensor systems for hydrogen peroxide, ethanol, and glucose detection and quantification. Feasibility of the innovative sensor concept was fully demonstrated through the development of calibration curves for each of the three analytes, and by demonstration of fiber optic transmission of sensor chemiluminescence to a remotely located PMT using a fiber optic waveguide.

Example 13
Operation of Basification Modules

Solid phase basification (SPB) beds containing crystalline $CaCO_3$ and $MgO$ were tested. A 1.0 $cm^3$ bed of $CaCO_3$ particles, sized between 100 and 1000 µm, was challenged with a 2.0 mL/min flow of DI water. This resulted in an effluent pH of 9.7. This unbuffered basic solution was then fed into a 0.5 $cm^3$ packed bed of crystalline luminol. The SPB-luminol combined effluent pH dropped to ~7, a value which is clearly too low for chemiluminescent reactions to proceed efficiently. By placing another $CaCO_3$ bed downstream from the luminol bed, the combined effluent pH increased to 9.7. This pH value is marginal for efficient chemiluminescence. Increasing the $CaCO_3$ bed volume to 10 $cm^3$ increased the empty bed contact time by a factor of ten, but had little impact on the effluent pH. Due to the high pH (10–11) required for efficient chemiluminescence, another SPB material was investigated.

Figure 15:
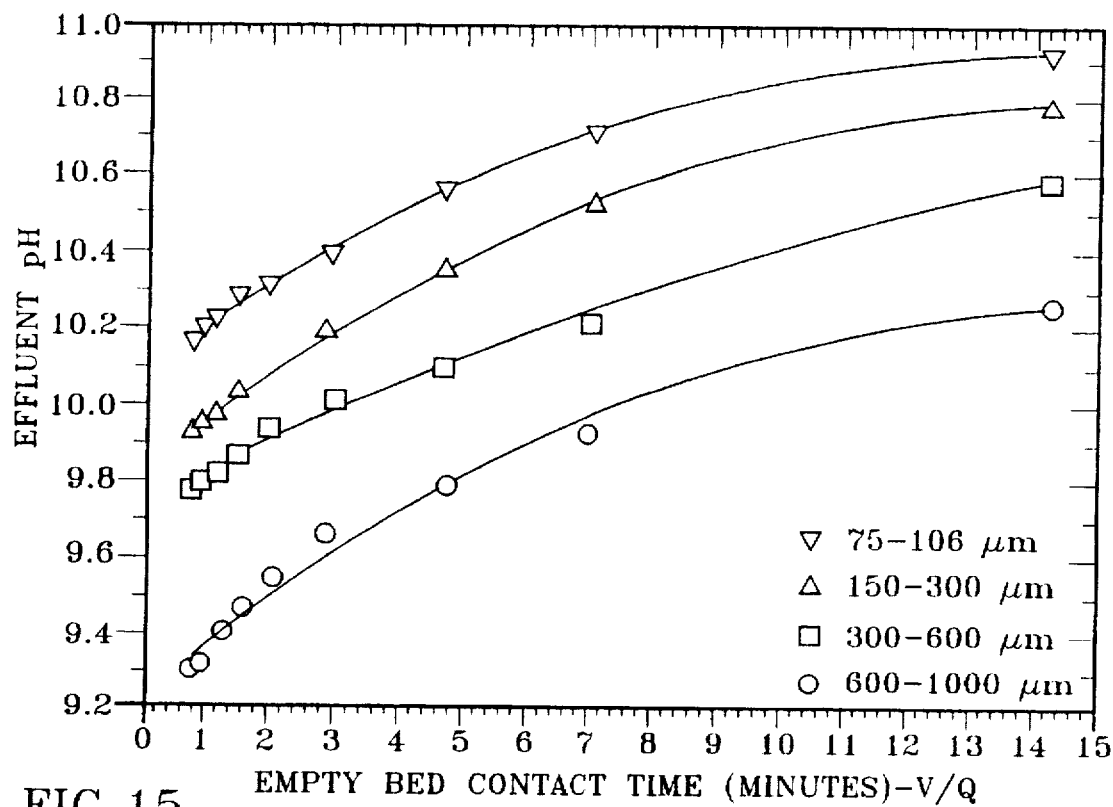
FIG. 15 graphically illustrates the dependence of effluent pH on the contact time for varied MgO particle size fractions.

Previous experience has shown that SPB beds containing $CaCO_3$ are less basic than $MgO$ by ~0.5 pH units. For this reason, a series of 1.4 $cm^3$ $MgO$ beds were prepared containing four different particle size fractions: 75–106, 150–300, 300–600, and 600–1000 µm, respectively. Each $MgO$ bed was then challenged with DI water at varied flow rates, corresponding to a range of empty bed contact times between 1–15 minutes. The results, shown in FIG. 15, clearly indicated that effluent pH was directly proportional to contact time and inversely proportional to particle size. Based on these data, the 75–106 µm particle size fraction was selected for testing in series with a luminol bed at a flow rate of 2 mL/min. The resultant pH was ~7.5 for the 2.5 $cm^3$ MgO-0.5 $cm^3$ luminol configuration. When a second 5.0 $cm^3$ MgO bed was placed downstream from the luminol bed, effluent pH increased to 10.3. This pH value was judged much better for promoting efficient luminol chemiluminescence. As a result, the MgO bed was selected for use in the SPB module.

Example 14
Solid Phase Module for Controlled Release of Luminol

The controlled release of luminol into the sample stream using an inline solid phase module greatly simplified the analytical process. The module must release enough luminol so that the quantitative chemiluminescent reactions can proceed over the desired concentration range for the target analyte. The module must also exhibit favorable stability and life characteristics so that near constant aqueous luminol levels can be sustained over prolonged periods of continuous flow. Two main approaches to achieving these results were taken, immobilization of luminol on CPG, and the use of packed beds of luminol crystals.

Figure 16:
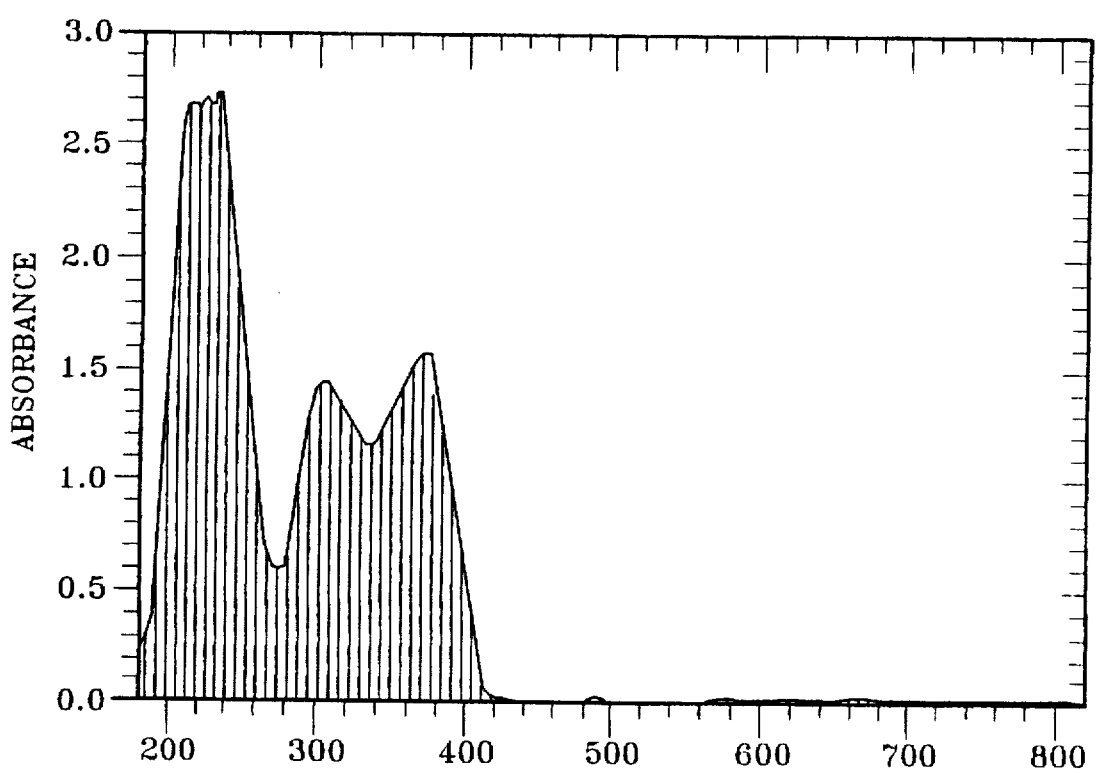
FIG. 16 graphically illustrates the ultraviolet-visible spectrum of 4.0 mg/L aqueous luminol.
Figure 17:
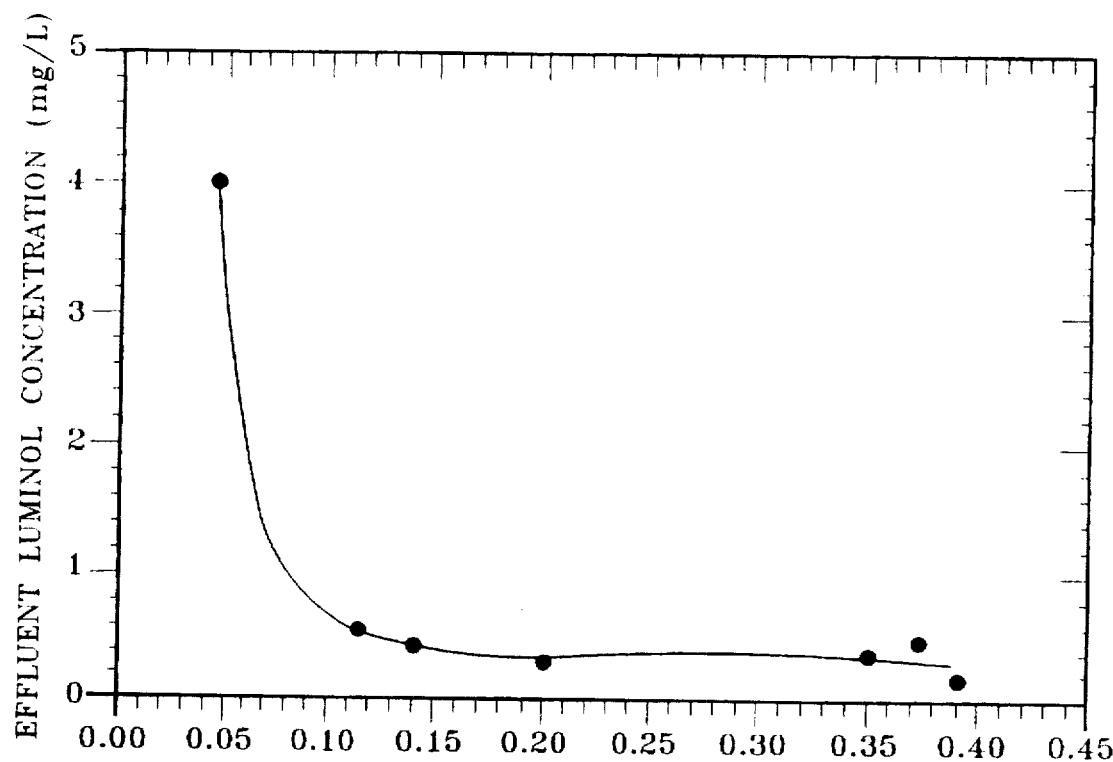
FIG. 17 is a washout curve of luminol immobilized on CPG showing the effluent luminol concentration as a function of deionized (DI) water throughput.

Luminol was immobilized on CPG via a silane linkage which included two imine bonds, as described in Example 2. These imine bonds are subject to hydrolysis reactions which are capable of slowly releasing luminol into an aqueous medium. Luminol was quantified using UV absorbance at 356 nm. A UV-visible absorbance spectrum for luminol in aqueous solution is shown in FIG. 16. By determining aqueous luminol levels before and after immobilization, loadings of 19.3 mg per gram of CPG were obtained. A 1.5 $cm^3$ bed was prepared and used to determine the relationship between aqueous luminol concentration and cumulative volumetric throughput (washout characteristics), at flow rates between 1–2 $cm^3$/min. The results of this experiment are shown in FIG. 17. Luminol immobilized in this manner exhibited both a short bed life and insufficient aqueous concentrations for use in the chemiluminescent biosensor application.

Example 15
Recrystallized Luminol

Figure 18:
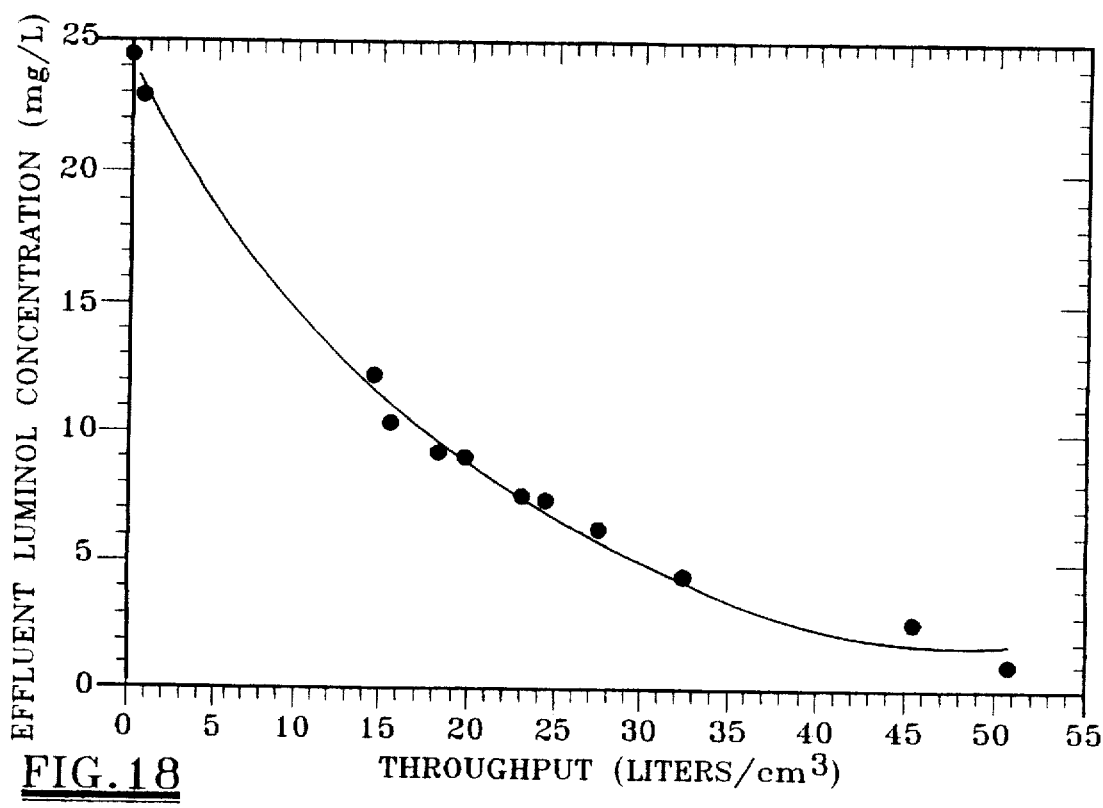
FIG. 18 is a washout curve of a crystalline luminol module showing the effluent luminol concentration as a function of DI water throughput.

Luminol is sparingly soluble in aqueous solutions, and for this reason is compatible with use in a solid phase module. Luminol is commercially available as a fine powder which is not usable for an in-line module due to the inordinately high inlet pressures required to sustain flow. Crystalline luminol with a more favorable particle size distribution was obtained by recrystallization from the vapor phase inside a tube furnace. A 0.5 $cm^3$ bed of crystalline luminol was prepared and used to determine the washout characteristics of this material with a DI water influent at flow rates between 1.6–2.0 $cm^3$/min. As shown in FIG. 18 higher effluent luminol concentrations were obtained than for the bed of luminol immobilized on CPG in Example 14. Also the symmetry of the washout curve indicates the potential for a much longer life than that seen for the immobilized luminol in Example 14.

The same bed of crystalline luminol was subsequently challenged with the effluent from a SPB bed. The effluent luminol concentration ranged between 42–59 mg/L. The solubility of luminol is known to be strongly pH dependent. The drop in pH from 10.3 to 7.5 after passage through the luminol bed indicates pH control of the dissolution process. Under continuous flow conditions, small variations in the pH of the water produced by the SPB bed produced only minor variations in aqueous luminol concentration even though the bed size was continually decreasing throughout the experiments. Evidently, the quantity of luminol that dissolves depends more on the influent pH than on the bed size (contact time). In the present application, the aqueous luminol concentration can be controlled by the pH adjustment of the SPB to produce a nearly constant level for prolonged periods of sustained flow. This behavior is ideal for application in reagentless chemiluminescent biosensors.

Example 16
Chemically Catalyzed Chemiluminescence Detection

Figure 19:
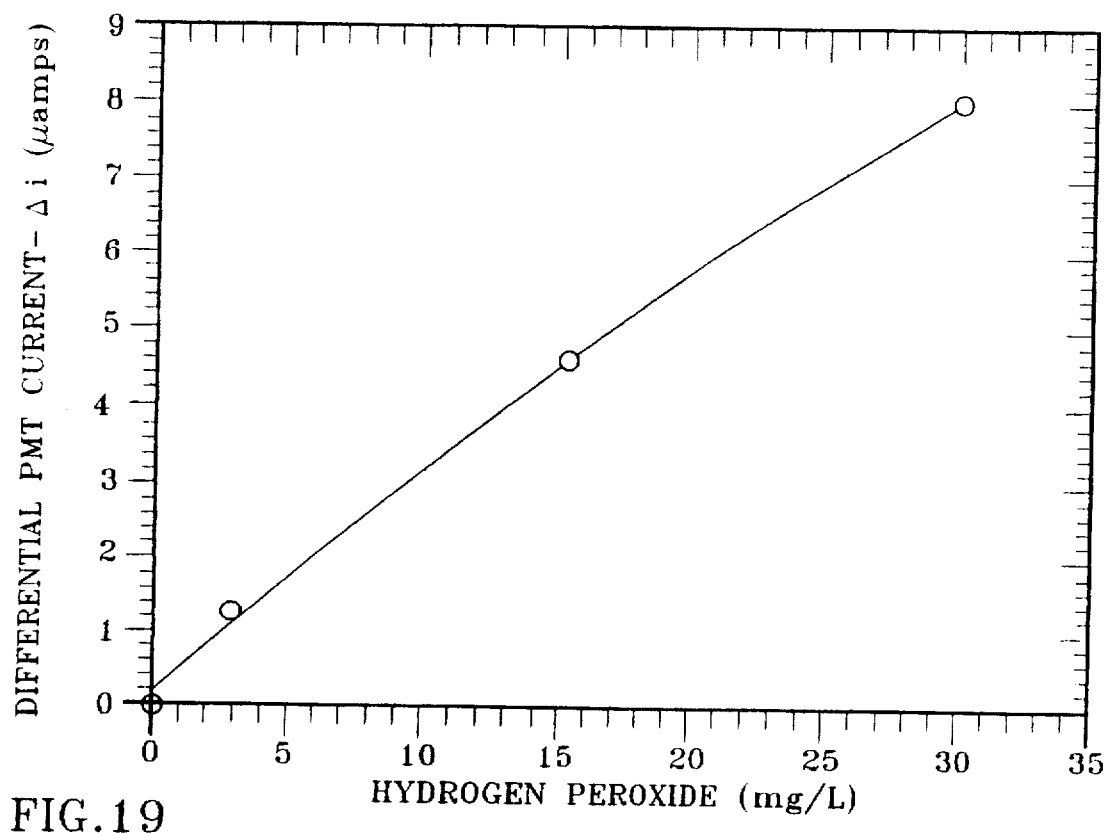
FIG. 19 is a graph of the chemically catalyzed $H_2O_2$ chemiluminescence for aqueous reagents plotting the differential photomultiplier tube (PMT) current as a function of hydrogen peroxide concentration.

Chemically catalyzed chemiluminescence was first investigated using prepared aqueous reagents. DI water was basified by passage through a SPB bed. Luminol dissolved in an ethanol-dimethyl sulfoxide mixture, and aqueous $Cu^{++}$ catalyst was added to the basified solution. Hydrogen peroxide was also mixed with the luminol-catalyst solution just prior to injection into the chemiluminescent chamber adjacent to the PMT. This ensured that the chemiluminescence was confined within a small volume in close proximity to the PMT. A calibration curve for $H_2O_2$ in the concentration range between 0–30 mg/L obtained using this method is given in FIG. 19.

Figure 20:
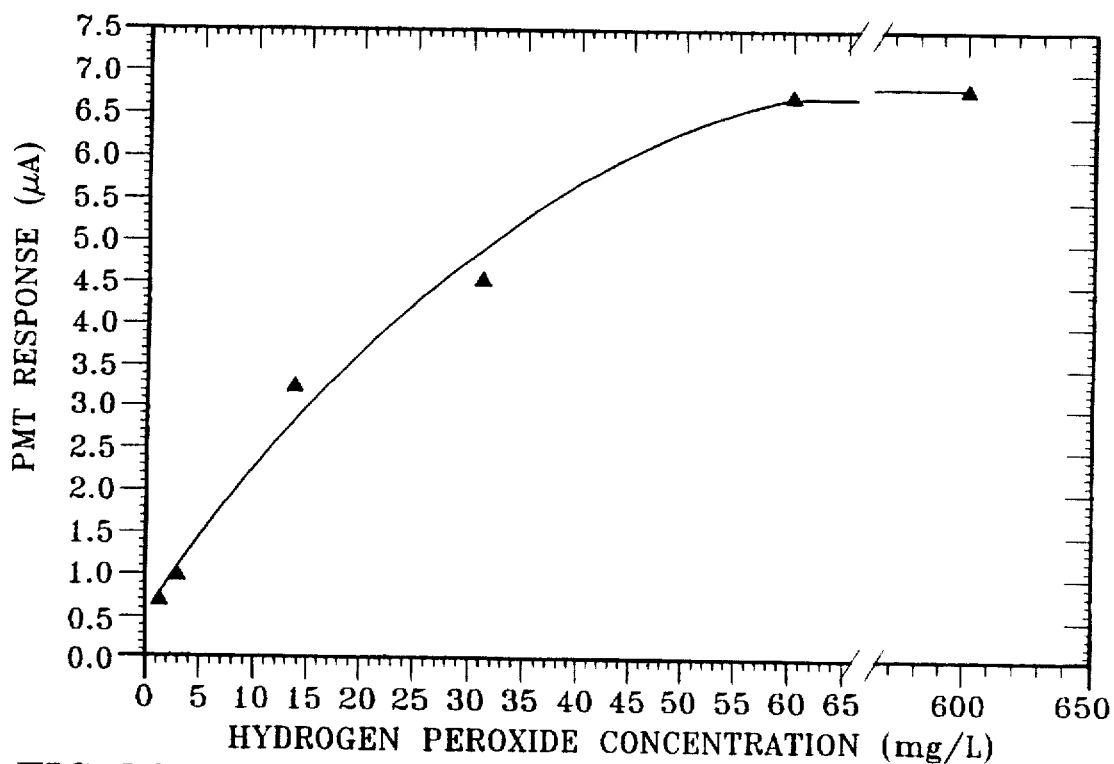
FIG. 20 is a graph of the chemically catalyzed $H_2O_2$ chemiluminescence for solid reagent modules plotting the PMT response as a function of hydrogen peroxide concentration.

This was followed by similar experiments using SPB and crystalline luminol beds, with aqueous $Cu^{++}$ introduced into the basified luminol containing stream. The calibration curve for hydrogen peroxide over the concentration span between 0 and 600 mg/L generated using the solid phase modules is shown in FIG. 20. The substantial increase in the effective range for the solid phase reagent system over the liquid reagent system was most probably due to the increased pH of the solid phase system effluents. Differing amounts of $Cu^{++}$ between the two systems might also have been responsible, since the formation of the insoluble hydroxide is favored at these high pHs. The chemically catalyzed luminescence experiments demonstrated the quantitative utility of the chemiluminescent oxidation reaction between $H_2O_2$ and luminol, and also confirmed the adequacy of the PMT and the optical coupling between the cell and the detector. The results of these experiments also prompted the development of baseline compensation and amplification circuitry for the PMT output so that much lower levels of the target analytes could be detected and quantified accurately. Rather than measuring the PMT photocathode current in μAmps, subsequent experiments measured amplifier output in the mV range.

Example 17

ECL Detection

The first ECL experiment provided a greater than 30 fold improvement in the minimum detection limit of hydrogen peroxide over the previously used chemically catalyzed system. After three hours of operation, however, ECL system response decreased by a factor of approximately one third. Upon disassembly of the ECL cell, a discoloration of the foil electrode surface was noted. The formation of an oxide coating of the gold surface was suspected. The surface contamination was removed and the cell reassembled.

Figure 21:
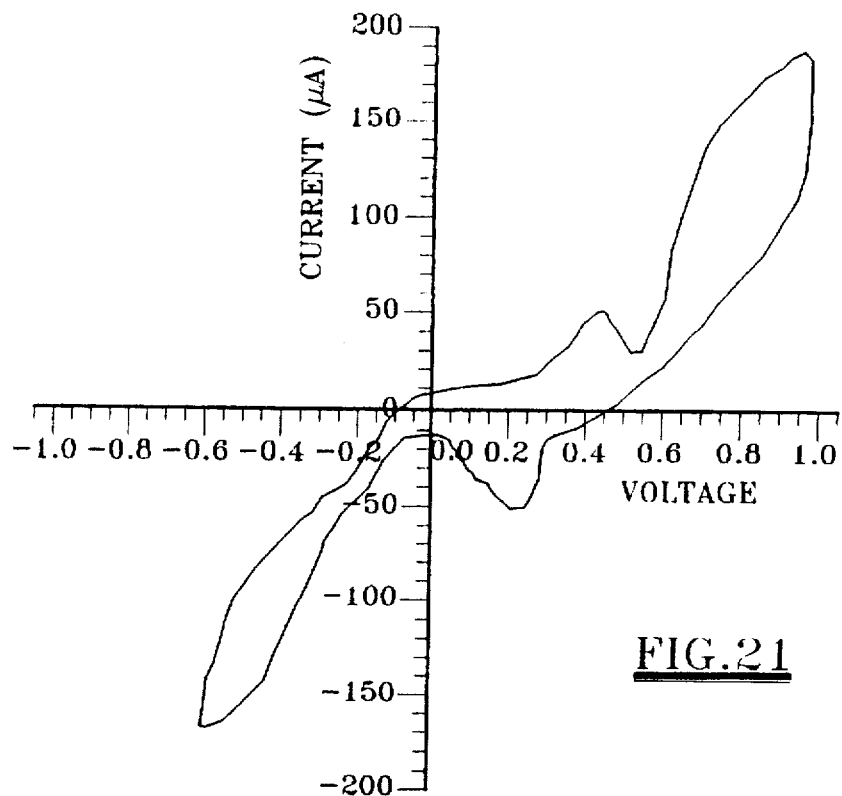
FIG. 21 is a cyclic voltammogram for an ECL cell gold electrode used in the biosensor of the present invention.

Cyclic voltammetry (CV) was performed using the potentiostat and ECL cell electrodes to determine precisely the sign and magnitude of electrode potentials which resulted in oxidation and reduction of the gold electrodes. The CV experiments were also expected to indicate if other oxidation-reduction reactions were occurring during ECL determinations. The voltage sweep rate was set at 20 mv/s, with the gold foil as the working electrode, the gold mesh as the counter electrode, and the Ag/AgCl reference electrode. The CV trace illustrated in FIG. 21 shows symmetrical oxidation-reduction reactions at +0.45 V and +0.175 V, with peaks at higher and lower voltages representing the oxidation and reduction of water.

These results indicated that the anode potential of +0.8 V applied to the foil was too high, promoting oxidation of the gold electrode. Continuous oxidation of the working electrode surface was judged responsible for degradation of the capacity of catalyze luminescence between luminol and hydrogen peroxide. A significant problem in the determination of suitable non-oxidizing electrode potentials originates from the low conductivity of the supporting electrolyte in the chemiluminescent biosensor configuration. This results in a significant (but unknown) potential drop between the reference and working electrode(s). As a result, the optimal voltage could only be determined empirically using the ECL cell and reference electrode. This was accomplished, and in subsequent runs, the anode voltage was reduced to +0.6 V.

Periodic switching of electrode parity was initially considered a more elegant solution to the gold oxidation problem. This was attempted when ECL cell performance degradation was first observed and abandoned because of instability in the output signal. The switching interval used varied between 0.2 to 30 seconds. Potential of both the working and counter electrodes was controlled relative to the reference. The lack of success for this approach most probably lies in the asymmetry between the electrodes.

During DC operation of the ECL cell, the PMT voltage reached its peak value within one minute of sample introduction. The primary delays in the detector response were due to the residence times within the solid phase beds and interconnecting tubing. Based upon these results it was concluded that continuous powering of the electrodes was not only unnecessary but also detrimental to long term sensor stability. Subsequently, the ECL electrodes were powered for one minute intervals at the end of which peak voltage was measured.

The combined effects of the new timing format and the reduced anode potential resulted in an increase in the viable operation time periods of over eight hours with only a 10% decrease in sensor response. Although the overall stability was much improved using the new operating procedures, this level of degradation was still considered unacceptable. For this reason development of suitable electrode regeneration methods were undertaken. This resulted in the adoption of a new polarity switching strategy in which the system was operated normally for six to eight hours, powering the electrodes intermittently for one minute intervals to perform analyses. The operational period was followed by one hour of continuous reversed polarity which was found to fully return the ECL electrodes to their original performance level. The system was operated in this manner for approximately 100 hours over a six week period with no discernible degradation in performance. Using this slow switching operational protocol, the ECL for the luminol-hydrogen peroxide reaction proved stable and reproducible.

Example 18

Immobilized Enzyme Beds

Both alcohol oxidase (AO) and glucose oxidase (GO) were immobilized on CPG and diatomaceous earth supports (DES) as described in Examples 1–3. AO beds were assayed for enzyme activity by the disappearance of ethanol and the appearance of acetaldehyde as determined by gas chromatography. GO beds were screened for enzyme activity using the appearance of hydrogen peroxide as measured using the horseradish peroxidase-o-dianisidine spectrophotometric method.

Assays of enzyme activities indicated that alcohol oxidase on DES and glucose oxidase on CPG catalyzed the highest rates of substrate conversion. AO on CPG displayed virtually no activity over a wide range of contact times. This result was somewhat surprising considering that the silanization technique has been used to immobilize a broad variety of enzymes to CPG. It may be that the reaction kinetics are drastically slowed by the tortuose interconnection between pores in this high surface area support, since most of the bound enzyme is present on internal surfaces. Such a pore diffusion limitation could be overcome using smaller sized CPG beads. AO on DES provided near stoichiometric conversion of 15.8 mg/L ethanol to acetaldehyde in a 10 $cm^3$ bed with a flow rate of 2 $cm^3$/min.

A 3 $cm^3$ bed of glucose oxidase on DES, challenged with a 6.4 mg/L D-glucose solution, showed no measurable activity at flow rates between 0.1 and 1.0 $cm^3$/min. In contrast, a 2.7 $cm^3$ bed of GO on CPG produced 0.4 mg/L of $H_2O_2$ from 6.4 mg/L of D-glucose at a flow rate of 0.1 cm³/min. This represented a $H_2O_2$ production efficiency of 33%. In comparison to AO, relatively low reaction rates were produced by immobilized GO. For this reason, the enzyme required relatively lower flow rates (increased contact time) to obtain an equivalent conversion efficiency. As a result, the flow ratios between the carrier stream and the analytical streams was very large at 11.7:1. The production of $H_2O_2$ using glucose oxidase was further limited by the relatively high levels of contamination by another enzyme (catalase) which promotes the decomposition of hydrogen peroxide. Fortunately, applications for glucose sensors predominantly require the quantitation of quite high levels.

While the alcohol oxidase enzyme was found to exhibit high levels of activity on DES, the efficient production of hydrogen peroxide for detection in the ECL cell required additional work. When a sufficiently large bed of AO on DES was challenged with an ethanol solution, complete conversion occurred producing hydrogen peroxide and acetaldehyde. Unfortunately, $H_2O_2$ is readily decomposed by transition metal impurities on the diatomaceous earth support. This resulted in poor recovery of the hydrogen peroxide from the immobilized enzyme bed. It was found that $H_2O_2$ recovery could be improved dramatically when flow rates and bed sizes were adjusted to give a better match between challenge ethanol concentrations and enzymatic activity. For application in the integrated ethanol chemiluminescent biosensor, a 1.2 cm³ AO bed was used at a flow rate of 3 cm³/min, corresponding to a carrier stream to analytical stream flow ratio of 1.5:1. In this configuration a challenge stream containing 395 µg/L of ethanol produced 33 µg/L of hydrogen peroxide. This corresponds to a $H_2O_2$ production efficiency of 11.3%.

Examples 19–21
Integrated Chemiluminescent Biosensor Tests

The components required to perform each unit operation were assembled into three integrated systems for quantitation of hydrogen peroxide, glucose, and ethanol, respectively. The solid phase basification beds, crystalline luminol beds, ECL cell, and detection methodology were identical in the three systems. The chemiluminescent biosensor systems differed as to the operational flow rate and the immobilized enzyme used.

Figure 22:
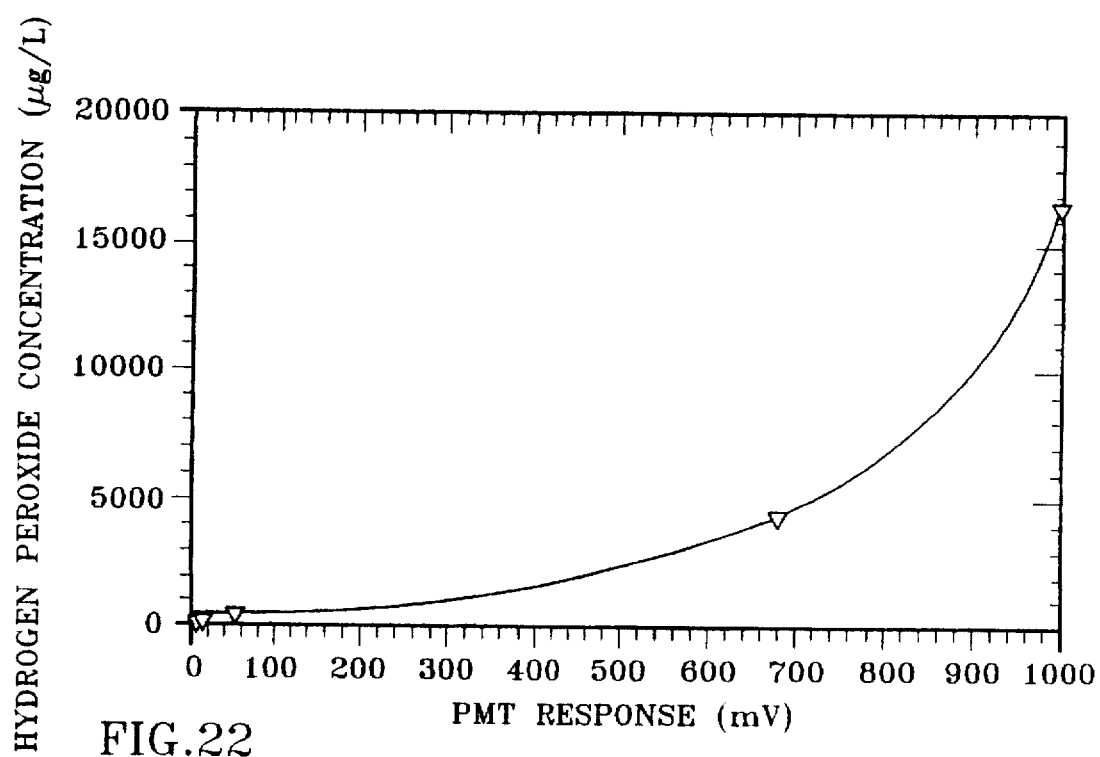
FIG. 22 is a hydrogen peroxide calibration curve for the integrated sensor system according to the present invention plotting hydrogen peroxide concentration as a function of PMT response.

The $H_2O_2$ sensor response was determined over the concentration range between 33–16500 µg/L (ppb). The resulting data were used to construct the sensor calibration curve shown in FIG. 22. The lower limit of detection for $H_2O_2$ is less than 33 µg/L (ppb), since the PMT output signal for this concentration was well above background. The $H_2O_2$ sensor was challenged with three replicates each of standards containing 33, 330, 3,300, and 16,650 µg/L (ppb), resulting in standard deviations (1σ) of 6.4, 7.3, 36.6, and 200 µg/L (ppb) respectively.

Figure 23:
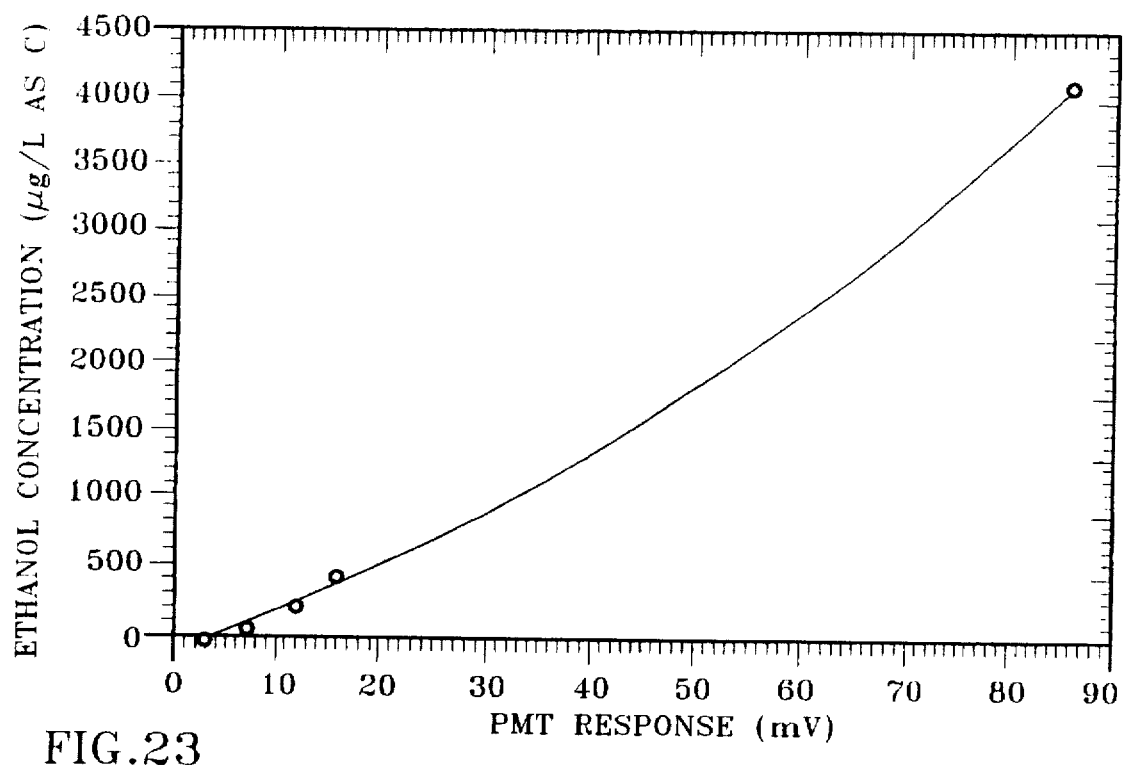
FIG. 23 is an ethanol calibration curve for the integrated sensor system according to the present invention plotting ethanol concentration as a function of PMT response.
Figure 24:
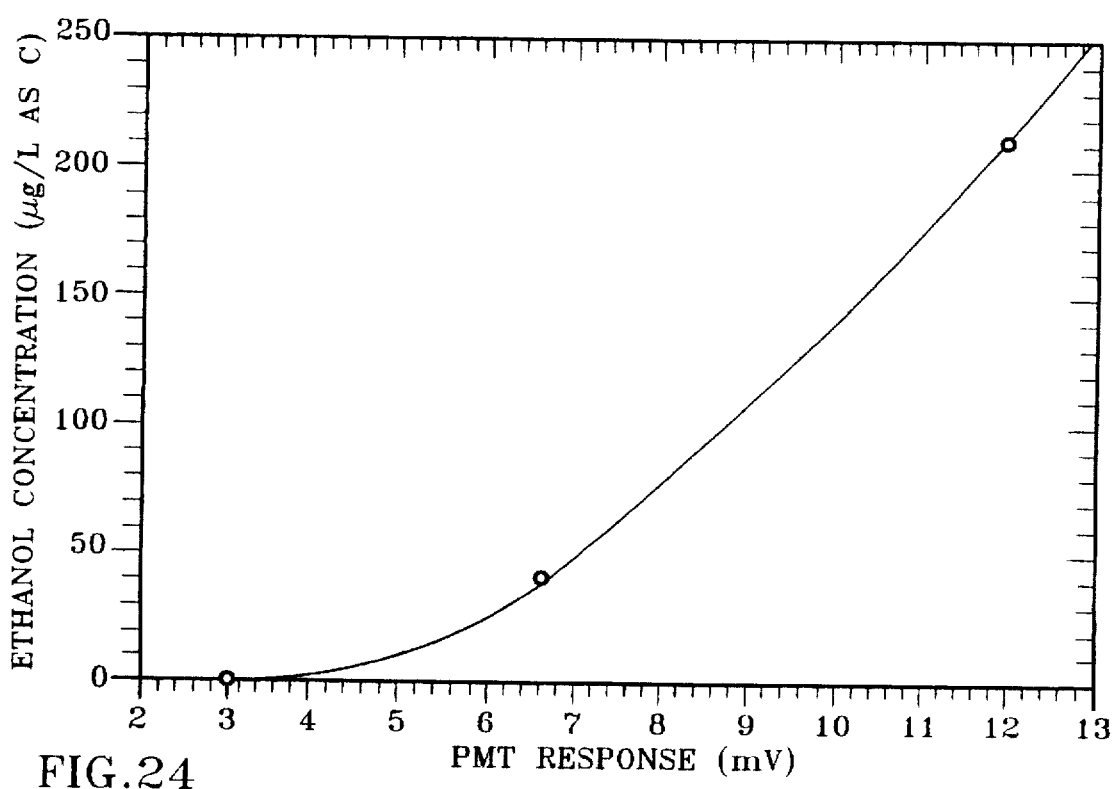
FIG. 24 is an ethanol calibration curve for the integrated sensor system according to the present invention plotting ethanol concentration as a function of PMT response over the ethanol concentration range from 0 to 250 µg/L.

Aqueous ethanol solutions ranging in concentration between 40 and 4114 µg/L (ppb) as C were determined using the integrated chemiluminescent ethanol biosensor. The resulting data were used to construct the smooth quadratic calibration curve over this range shown in FIG. 23. Because the ability to detect very low levels is an important feature of the ethanol biosensor system, an expanded scale version of this curve between 0 and 250 µg/L (ppb) is presented in FIG. 24. These data clearly demonstrate the sensitivity of this technique and the capacity to extend the lower limits of detection to even lower values with the current sensor configuration. The ethanol sensor was challenged with three replicates each of standards containing 40, 200, 410, and 4,100 µg/L (ppb), resulting in standard deviations (1σ) of 3.6, 17.0, 25.4, and 98.4 µg/L (ppb) respectively.

Figure 25:
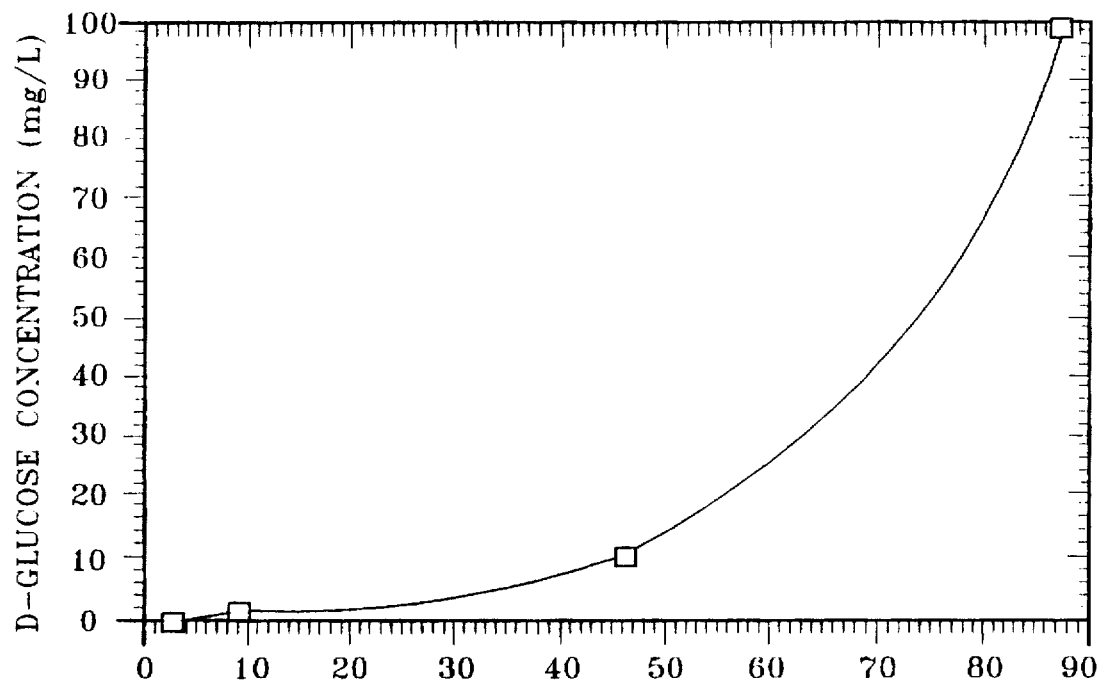
FIG. 25 is a D-glucose calibration curve for the integrated sensor system according to the present invention plotting D-glucose concentration as a function of PMT response.

Aqueous D-glucose solutions ranging in concentration between 1 and 100 mg/L (ppm) were analyzed using the integrated chemiluminescent glucose biosensor. The resulting data were used to construct the smooth quadratic calibration curve over this range shown in FIG. 25. The glucose sensor was challenged with three replicates each of standards containing 1.0, 10, and 100 mg/L (ppm), resulting in standard deviations (1σ) of 0.2, 0.6, and 8.1 mg/L (ppm), respectively. In contrast to ethanol sensors which require extremely low limits of detection, potential applications for glucose sensors, such as on-line monitoring of fermentation bioreactors, require the determination of relatively high glucose levels. Thus, the glucose sensor preferably has an upper limit of accurate quantitation of 5,000 mg/L.

Example 22
Fiber Optic Transmission of Chemiluminescence

Figure 26:
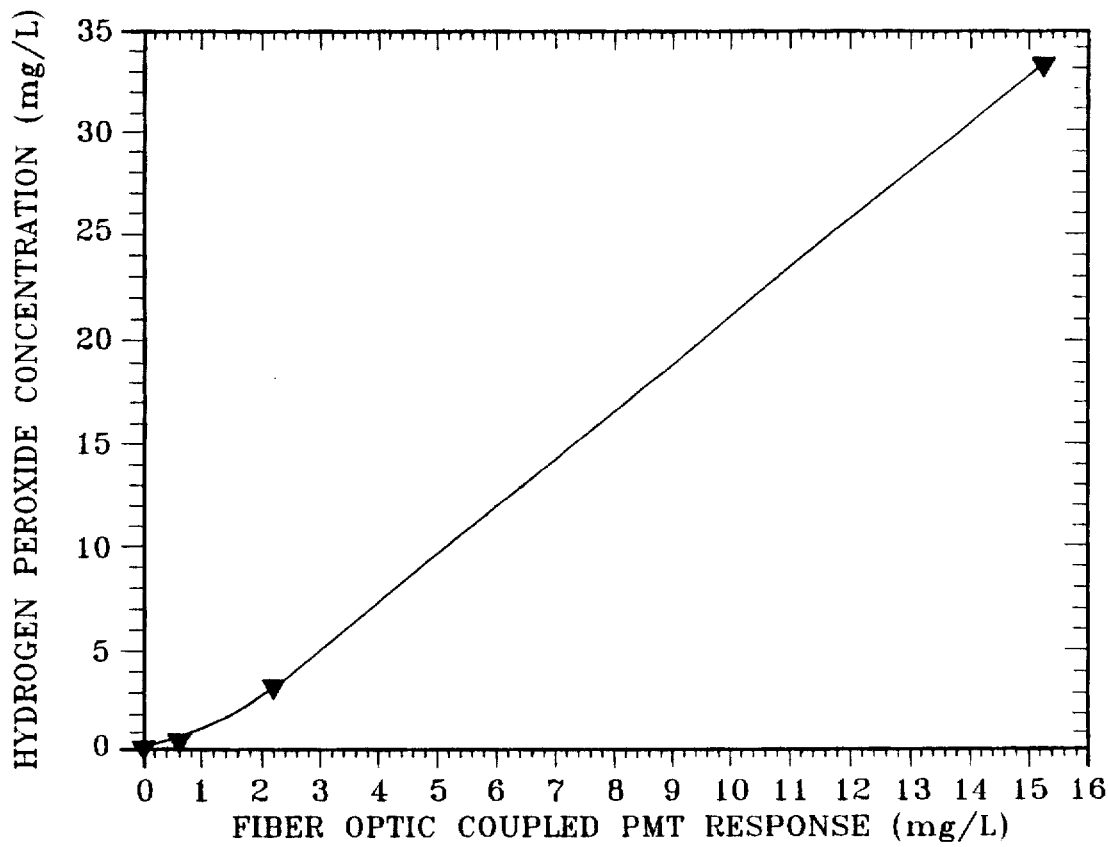
FIG. 26 is a hydrogen peroxide calibration curve for the integrated fiber optic sensor system plotting the hydrogen peroxide concentration as a function of the fiber optic coupled PMT response.

To demonstrate the transmission of a chemiluminescent signal to a remotely located detector, a 1.2 meter length of a fiber optic bundle composed of 50,000 fibers was optically coupled at opposite ends to the PMT photocathode, and to a transparent face of the ECL cell. Tests were conducted using the integrated hydrogen peroxide chemiluminescent sensor system. Aqueous hydrogen peroxide solutions with concentrations ranging between 0.33 and 33 mg/L were analyzed. The analytical results were used to construct the $H_2O_2$ calibration curve shown in FIG. 26. Using fiber optic transmission the PMT response was reduced by a factor of ~32 as compared to direct optical coupling of the PMT with the ECL. This reduction in signal intensity is clearly due to poorer collection efficiency and transmission losses associated with the fiber optic cable. It is believed that the losses can be drastically reduced by using an ECL cell which maximizes light transmission into the cone of acceptance of the fiber optic bundle.

Feasibility of the Fiber Optic Chemiluminescent Biosensor concept has been rigorously demonstrated. Calibration curves for ethanol, D-glucose, and hydrogen peroxide have been generated using fully integrated reagentless test systems. Ethanol concentrations as low as 40 µg/L have been detected. The height of the signal above the baseline for this concentration suggests that even lower levels could be detected using the current relatively crude embodiment of the present invention.

Detection limits are primarily determined by enzyme conversion efficiencies, dark current limitations, light leakage, detection circuitry, and background chemiluminescence.

Unit operations required for sensor operation have been developed sufficiently for demonstration of the principles of the present invention. These include pH adjustment using solid phase flow-through modules, immobilized enzyme catalyzed oxidation of ethanol and glucose to hydrogen peroxide, controlled release of luminol using a solid phase flow-through module, electrocatalyzed luminescence using a potentiostat and gold electrodes, fiber optic transmission of chemiluminescent emissions, and quantification of light intensity using a photomultiplier tube.

Of the two solid phase basification materials studied, MgO was found superior for the current application. MgO beds were shown to consistently provide the pH adjustment required for the chemiluminescent reactions. Two enzyme immobilization procedures were examined. The titanium activation procedure using diatomaceous earth for support resulted in the best level of activity and stability for alcohol oxidase. Glucose oxidase, on the other hand, performed better when immobilized on controlled porosity glass using the silanization technique. Depletion rates for luminol immobilized on controlled porosity glass were too great for this means for addition of the luminophore to be practical. This problem was overcome by development of recrystallization methods which allowed the use of packed beds of luminol crystals. The solid phase luminol beds were shown capable of sustained controlled release of the luminophore at a sufficient concentration for the sensor systems to function over a broad span of target analyte concentrations. The ECL cell fabricated from transparent polycarbonate, and using a gold foil working electrode, and a gold mesh counter electrode, was found to effectively initiate the reaction, between luminol and hydrogen peroxide at an applied potential of 0.6 volts. The ECL cell design was also found to adequately confine the reaction spatially for efficient collection of the light either directly by an optically coupled photomultiplier tube, or by transmission of the light through a fiber optic bundle to a remotely located photomultiplier tube.

Current requirements for reclaimed potable water specify a maximum of 500 µg/L TOC, with a maximum of 100 µg/L TOC as uncharacterized TOC. Previous technologies such as aqueous phase catalytic oxidation systems (APCOS) are certainly capable of meeting the 500 µg/L limit, but may have difficulty with the 100 µg/L limit depending upon the magnitude and composition of the influent organics. The problem of uncharacterized TOC can be diminished by using a strategic selection of chemiluminescent biosensors to characterize methanol, ethanol, ethylene glycol, 1,2-propanediol, lactic acid, and glycolic acid concentrations in the product water. These results taken together with formic, acetic, and propionic acid concentrations, determined using a membrane separation and specific conductance detection methodology, can provide characterization of the vast majority of organic contaminants known to occur in significant concentrations.

We claim:

1. A chemiluminescent biosensor for determining the presence of a target chemical in an aqueous sample stream, comprising:
    a solid phase basification module for basifying the aqueous sample stream, wherein the solid phase basification module comprises a bed of crystalline MgO particles;
    a solid phase luminol module for releasing luminol into the aqueous sample stream at a controlled rate, wherein the solid phase luminol module comprises a bed of crystalline luminol;
    a chemiluminescence cell for catalyzing reaction of the luminol and any hydrogen peroxide in the basified aqueous sample stream;
    a photomultiplier tube optically coupled to the chemiluminescence cell for detecting and measuring light emitted from the chemiluminescence cell, wherein the light emission measurement is a function of the quantity of hydrogen peroxide in the basified aqueous sample stream.

2. The biosensor of claim 1, further comprising an immobilized enzyme module for catalyzing oxidation of the target chemical in the aqueous sample stream to form hydrogen peroxide.

3. The biosensor of claim 2, wherein the enzyme is immobilized on diatomaceous earth or controlled porosity glass.

4. The biosensor of claim 2, wherein the enzyme is selected from glucose oxidase, alcohol oxidase, lactic acid oxidase, amino acid oxidase, glutamate oxidase, lysine oxidase, oxalate oxidase, polyphenol oxidase, cholesterol oxidase, xanthine oxidase, L-α-glycerol phosphate oxidase, choline oxidase, ascorbate oxidase, and sulfite oxidase.

5. The biosensor of claim 1, further comprising:
    a carrier line for passing water in series through the basification and luminol modules to form a basified carrier stream containing luminol; and
    an analyte line for introducing the aqueous sample stream into the carrier stream to form a chemiluminescent mixture for feed to the chemiluminescence cell.

6. The biosensor of claim 5, further comprising an immobilized enzyme module in the analyte line for catalyzing oxidation of the target chemical to form hydrogen peroxide in the aqueous sample stream.

7. The biosensor of claim 1, wherein the chemiluminescence cell is chemically catalyzed by a supplemental oxidant.

8. The biosensor of claim 1, wherein the chemiluminescence cell is electrocatalyzed.

9. The biosensor of claim 8, wherein the chemiluminescence cell comprises an electrolytic cell including an anode, a cathode and a reference electrode.

10. The biosensor of claim 9, wherein the chemiluminescence cell includes a potentiostat for maintaining a desired potential between the anode and cathode relative to the reference electrode.

11. The biosensor of claim 10, wherein the chemiluminescence cell comprises front and back plates spaced apart by a gasket, a foil electrode adjacent the back plate and a mesh electrode adjacent the front plate, wherein the front plate is translucent and the photomultiplier tube is optically coupled to the front plate.

12. The biosensor of claim 11, wherein the anode voltage is maintained below 0.8 volts and the chemiluminescence cell includes means for intermittently applying voltage to the electrodes for a period of time sufficient to reach a peak voltage in the photomultiplier tube, and a polarity switches for periodically reversing the polarity of the electrodes to regenerate the electrodes.

13. The biosensor of claim 11, wherein the gasket defines a tortuous flow path between the electrodes from a fluid inlet to a fluid outlet.

14. The biosensor of claim 11, further comprising a fiber optic cable having opposite ends optically coupled to the front plate of the chemiluminescence cell and the photomultiplier tube.

15. A method for determining the presence of a target chemical in an aqueous sample stream, comprising the steps of:
    operating the chemiluminescent biosensor of claim 1 to measure the light emitted when the basified aqueous sample stream containing luminol is fed to the chemiluminescent cell; and
    comparing the measured light emission with a calibration curve to quantify the amount of the target chemical in the aqueous sample stream.

16. A method for determining the presence of a target chemical in an aqueous sample stream, comprising the steps of:
    passing the aqueous sample stream in series through the immobilized enzyme module, solid phase basification module, solid phase luminol module and chemiluminescence cell of the biosensor of claim 2, wherein the chemiluminescence cell is an electrolytic cell including an anode, a cathode and a reference electrode;
    applying a voltage across the anode and cathode;
    obtaining a measurement from the photomultiplier tube; and
    comparing the measurement from the photomultiplier tube with reference measurement obtained from a reference stream containing a known amount of the target chemical to determine the amount of the target chemical in the aqueous sample stream.

17. The method of claim 16, wherein the enzyme is glucose oxidase and the target chemical is glucose.

18. The method of claim 16, wherein the enzyme is alcohol oxidase and the target chemical is ethanol.

* * * * *